(12) United States Patent
Owsley

(10) Patent No.: US 11,412,984 B1
(45) Date of Patent: Aug. 16, 2022

(54) SYSTEMS, APPARATUSES, AND METHODS FOR ESTABLISHING SENSOR POSITIONS ON A HUMAN'S BODY WITH AN ARTICULATED CONFORMAL ARRAY

(71) Applicant: PHONOFLOW MEDICAL, LLC, Gales Ferry, CT (US)

(72) Inventor: Norman Lee Owsley, Gales Ferry, CT (US)

(73) Assignee: PHONOFLOW MEDICAL, LLC, Gales Ferry, CT (US)

( * ) Notice: Subject to any disclaimer, the term of this patent is extended or adjusted under 35 U.S.C. 154(b) by 0 days.

(21) Appl. No.: 17/220,863

(22) Filed: Apr. 1, 2021

(51) Int. Cl.
*A61B 5/02* (2006.01)
*A61B 5/029* (2006.01)
*A61B 5/026* (2006.01)
*A61B 5/00* (2006.01)
*A61B 5/11* (2006.01)

(52) U.S. Cl.
CPC ............ *A61B 5/684* (2013.01); *A61B 5/1102* (2013.01); *A61B 5/6844* (2013.01); *A61B 2562/0219* (2013.01); *A61B 2562/164* (2013.01)

(58) Field of Classification Search
CPC ........ A61B 2562/0204; A61B 5/02007; A61B 5/026; A61B 5/7203; A61B 5/7246; A61B 5/7257; A61B 7/00
See application file for complete search history.

(56) References Cited

U.S. PATENT DOCUMENTS

2014/0187971 A1* 7/2014 Owsley .................. A61B 5/026
600/479

* cited by examiner

*Primary Examiner* — Jon Eric C Morales
(74) *Attorney, Agent, or Firm* — Peloquin, PLLC; Mark S. Peloquin, Esq.

(57) ABSTRACT

Apparatuses, methods, and systems are disclosed to establish sensor locations on a human's body. A reference plane structure establishes a measurement datum. A plurality of fixtures is provided. Each fixture of the plurality contains at least one sensor and provides a tensile preload to the at least one sensor. A first fixture of the plurality is supported by the reference plane structure. A location on the human's body is associated with each sensor. Each location on the human's body is established using the measurement datum and a contact point of each sensor. The plurality is articulated together to conform to a shape of the human's body such that, when in use, each sensor is in contact with the human's body, and each location is defined by the measurement datum and a contact point of each sensor.

33 Claims, 21 Drawing Sheets

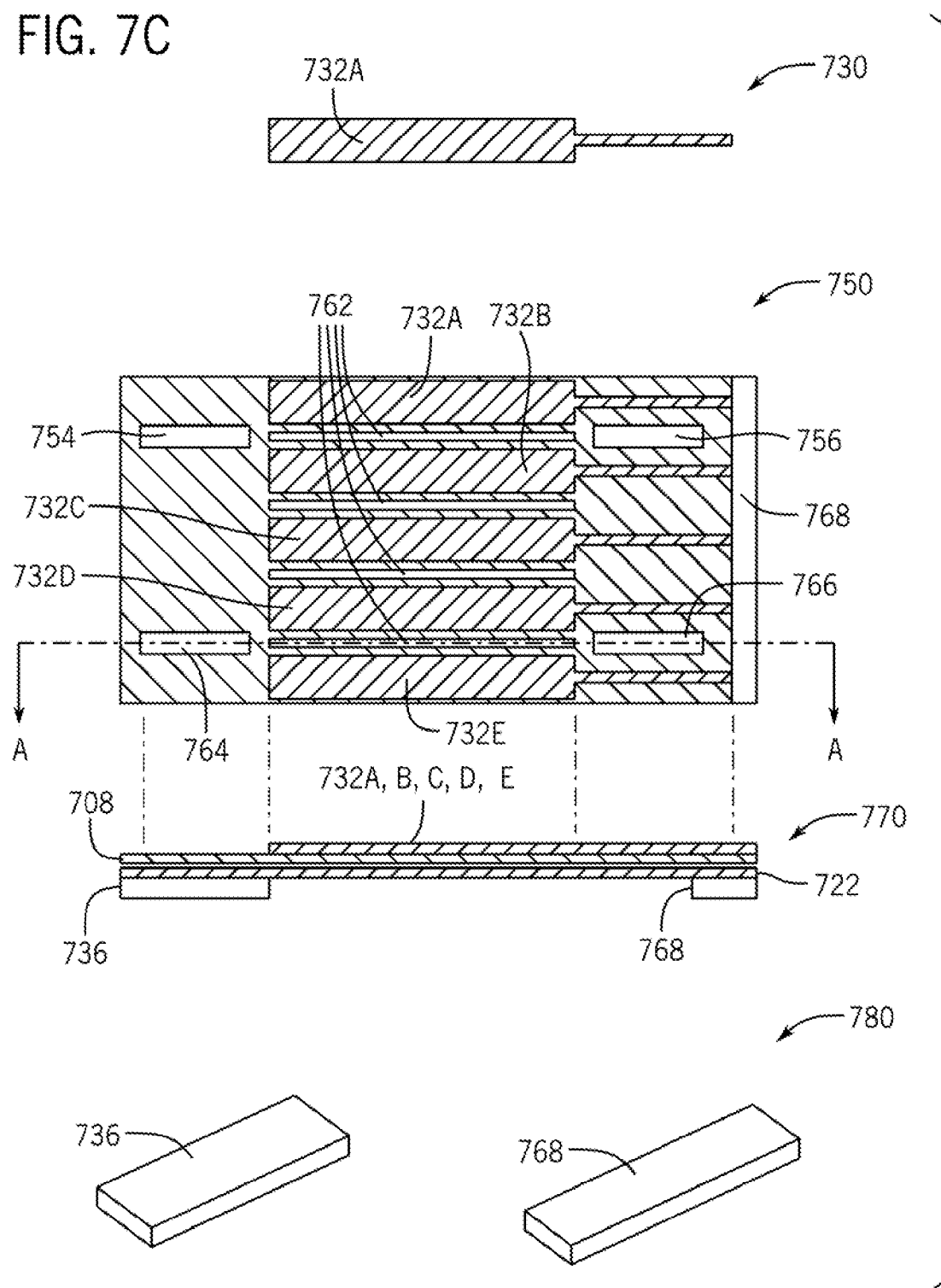

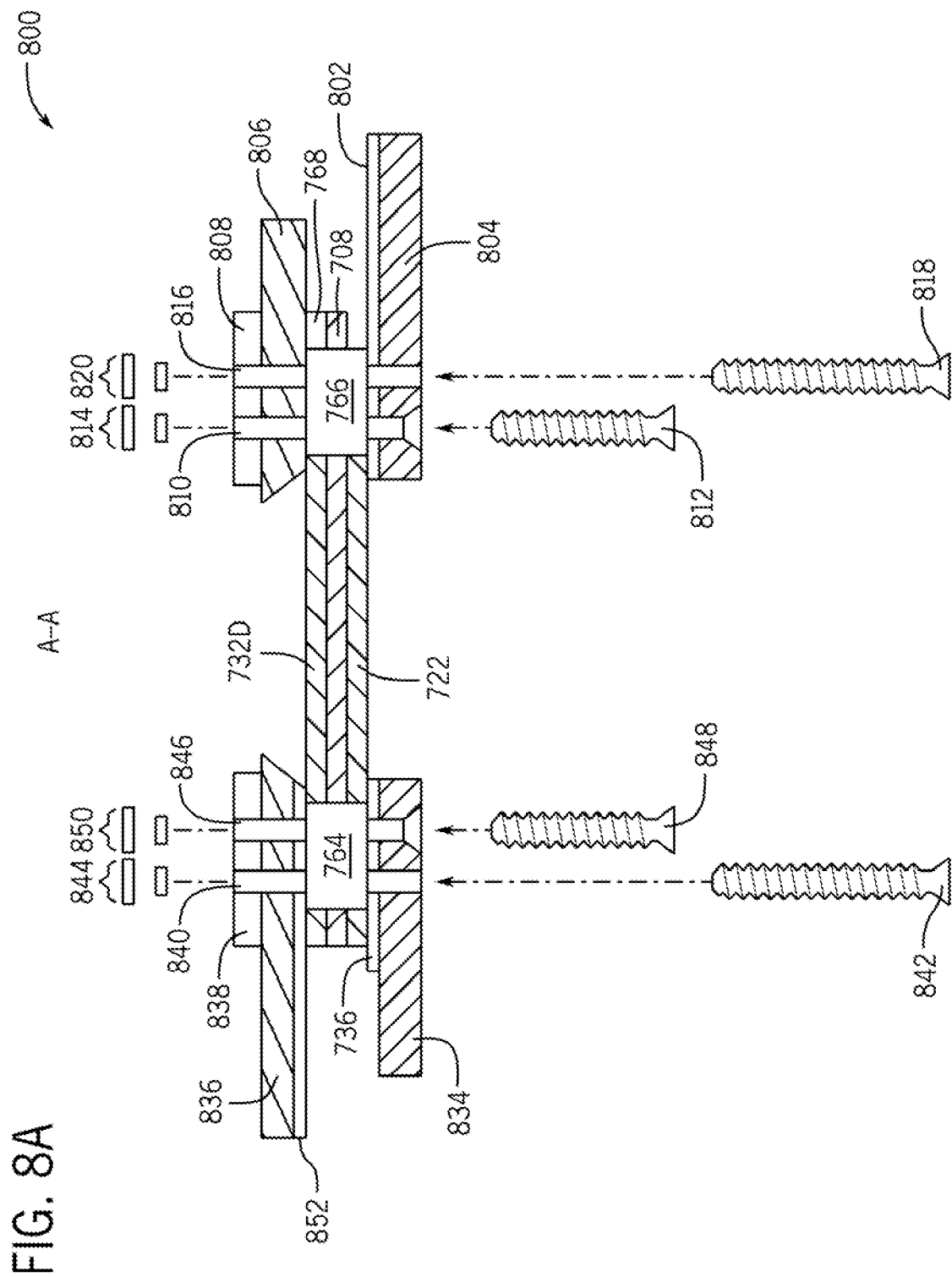

SYSTEMS, APPARATUSES, AND METHODS FOR ESTABLISHING SENSOR POSITIONS ON A HUMAN'S BODY WITH AN ARTICULATED CONFORMAL ARRAY

BACKGROUND OF THE INVENTION

1. Field of the Invention

The invention relates generally to detecting and processing vibrational cardiac data, and more specifically to systems, apparatuses, and methods used for the measurement of blood flow turbulence-induced sources of vibrational cardiac data related to coronary and peripheral artery disease.

2. Art Background

Coronary artery disease is a primary precursor of heart attacks, which is a leading cause of death in the United States. Coronary artery disease is characterized by a deposition of plaque within the wall of a coronary artery, frequently resulting in a condition referred to as an occlusion, in which case blood flow may be restricted and the oxygen supply to the heart muscle may be decreased. Such a deposition of inwardly intrusive plaque is also referred to as a stenosis. Coronary artery disease can result in a heart attack and subsequent physical injury and possible death. This can present a problem.

Heart valve incompetence is characterized by abnormal blood flow through any of the four valves of the heart. Valve calcification, stenosis and valve leakage are variants of heart valve degeneration that can induce specific blood flow turbulence and vibration in the valve leaflets and contiguous valve tissue. This can present a problem.

It is known that blood flow can become increasingly turbulent as the blood passes through either an occluded artery or an incompetent valve. Turbulent blood flow provides a source of vibrational excitation within the body. The vibrational excitation causes elastic energy waves to propagate through the body and provides a motion field that can be measured at the surface of the body. Normal body functions such as breathing and the normal opening and closing of the heart's valves provide high levels of background noise relative to the magnitude of the vibrational energy resulting from blood flow induced vibration points. Such high levels of background noise can present a problem.

Currently, Coronary Artery Disease (CAD) is diagnosed post-symptomatically with some combination of a stress perfusion test and angiographic imaging. The stress test can be insufficiently accurate for either a positive or a negative diagnosis of CAD. The angiogram is costly, invasive, and places the patient at risk of injury due to complications that can arise during a required catheterization procedure. Moreover, both stress and angiographic procedures involve patient exposure to radiation. All of this can present problems.

It is known that heart valve leaflets can become calcified over time. Such calcification stiffens the valve and impairs the efficiency of flow through the valve and contributes to ancillary dysfunction of a person's cardiovascular system and can present problems to a person's state of cardiovascular health. All of this presents problems.

People have different physiological body types. Measurement of vibrations over an extended region of the body surface for which that surface may present different contours from one patient to another presents problems for vibration measurement systems because of the non-uniformity between body types. All of this presents problems.

Some sensors that measure and record body vibration by making contact with the body can depend on maintaining a minimum tension in a flexible piezoelectric vibration pickup. If this minimum tension is not maintained with relative uniformity over a plurality of sensors that are contacting the surface of the body, over the selected extended region of the body, then performance of the apparatus may be degraded. All of this presents problems.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

FIG. 7C illustrates another arrangement of the multi-sensor PVDF film array, described above in FIG. 7B, according to embodiments of the invention.

FIG. 8A illustrates film sensor clamping, according to embodiments of the invention.

DETAILED DESCRIPTION

In the following detailed description of embodiments of the invention, reference is made to the accompanying drawings in which like references indicate similar elements, and in which is shown by way of illustrative examples, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense, and the scope of the invention is defined only by the appended claims.

The apparatuses, systems, and methods are described for establishing sensor positions on a human's chest or body. The sensor positions are used for processing the data that is used for detecting, locating and classifying vibrational cardiac data in a human. In one or more embodiments, the vibrational cardiac data arise from turbulent blood flow in a coronary artery. In another embodiment the vibrational cardiac data arise from blood flow through a heart valve. In yet another embodiment, vibrational data is simulated and measured using a human phantom with an occlusion.

Figure 1A:
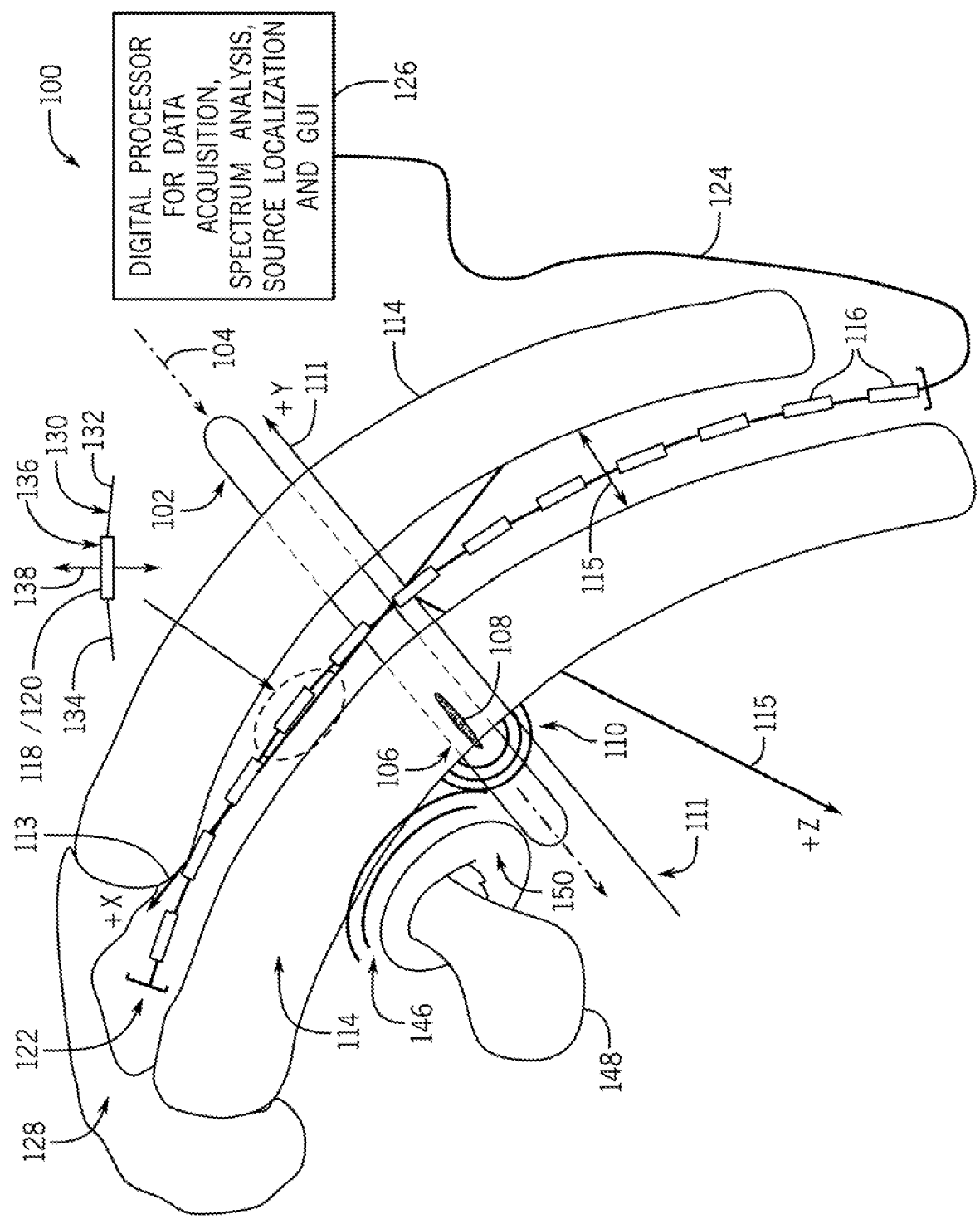
FIG. 1A illustrates the use of a body vibration sensing apparatus, according to one embodiment of the invention.

FIG. 1A illustrates the use of a body vibration sensing apparatus generally at 100, according to one embodiment of the invention. With reference to FIG. 1A, a section of a human thorax containing two ribs at 114 adjoined to the sternum at 128 and separated by an intercostal space at 115 are graphically represented. Under the ribs both a coronary artery segment at 102 having a flow of blood at 104 and a mitral valve with blood flow at 148 with flow induced valve leaflet vibration at 146 and 150 are represented. The directional flow of arterial blood 104 can interact with a coronary artery lesion 108 and cause an excitation 110 of the artery wall by known physical means, which include transition to turbulent flow 106 and the corresponding application of forces normal to the inner wall of the coronary artery. Such excitation of the coronary artery wall results in vibrational energy 110 propagating to the surface of the human chest through the intercostal space at 115. Likewise, valve leaflet calcification at 150 can result in leaflet stiffness that, in turn, amplifies turbulence-induced vibration.

In this description of embodiments, the term "sensor" is synonymous with the terms "channel" or "sensor channel," whereby a separate measurement for each channel is contemplated. Additionally, the term "sensor" is synonymous with the terms "transducer" or "sensing transducer." Thus, a first sensor's output (a first channel) and a second sensor's output (a second channel) are each available for analysis and each represents a separate measurement of a field quantity of interest, such as the vibration field in a human's body. As will be noted by those of skill in the art, in some instances, it might be advantageous for measurement sensitivity to mathematically combine together, in series or parallel, several sensors into a single channel. Such combinations can be made within the scope of the descriptions provided herein. However, to simplify the discussion, "sensor" will be understood to be synonymous with the terms "sensor channel," "channel," "transducer," or "sensing transducer."

In FIG. 1A, a conformal array of sensors at 116 measures the vibration of the surface over the intercostal space 115 and acquires vibrational cardiac data thereby. The array of sensors 116 is made up of a general number of N(≥2) sensors (sensing transducers or transducers). In one embodiment, the number N equals 15 and the spacing between adjacent transducers is one-quarter inch (0.25"). Those of skill in the art of discrete sensor array design will recognize that the array of N sensors at 116 can be configured with a different number of sensors, a different sensor width, different sensor spacing, and different vibration transducer types, such as but not limited to; strain sensors, accelerometers, as well as non-contact sensors, etc. The examples given herein is provided merely for illustration of a specific design and do not limit embodiments of the invention.

The representational view of the human in FIG. 1A presents a non-homogeneous media through which the vibrational energy 110 propagates and contains various structures such as ribs 114 as well as lungs, organs, interfaces, muscles, fat, and skin tissue. The vibrational energy propagates through the non-homogeneous media with a composite, average vibration wave propagation speed and is measured on the skin surface by the array of N sensors 116. In various embodiments, it can be desirable to place the array of sensors 116 over a person's heart and above an intercostal space between adjacent ribs to facilitate sensing of the vibrational energy with minimal anatomically related inhomogeneity.

In one embodiment, each sensor of the array of sensors 116, in contact with the body surface, is made from a strip of polyvinylidene fluoride (PVDF) film. In one example, each strip of PVDF film measures 0.75 inches long, between attachments to a chassis 122, and 0.1875 inches wide. At the midpoint of each strip of PVDF film, a rigid pad is placed to provide an area of contact between the skin surface and the strip of PVDF film. An example of one such sensor from the array of sensors 116 is illustrated by a strip of PVDF film 130, having a first end 132 and a second end 134 (which are attached to a fixture as described below in the figures that follow) and a pad 136 that makes contact with the skin surface. In one embodiment, the diameter of the pads is 0.1875 inches and the thickness of the pads is 0.0625 inches. In one or more embodiments, the sensitivity of the PVDF film along its major axis is 22176 V/unit strain for a PVDF film thickness of 0.028 millimeters. The sensitivity of PVDF film can vary, and the value of 22176 V/unit strain is given merely for example, with no limitation implied thereby. The PVDF film generates a voltage in response to strain imparted from the vibrating motion 138 of the skin surface. In one embodiment, the fixtures are made out of metal such as aluminum, in other embodiments, the fixtures are made out of plastic or another material sufficient to provide the necessary anchor points for the strips of PVDF film.

Each sensing transducer is in electrical contact with at least one preamplifier 120 using connection 118. It is advantageous to place a preamplifier proximate to its sensing transducer in order to minimize the addition of excessive electronic noise. Additional amplification stages can be used and in one embodiment the outputs from the preamplifiers 120 are passed to a bank of amplifiers. In one embodiment, the outputs of the sensing transducers (array 116) are carried in a cable bundle 124 and are processed in a data acquisition system 126 that can contain a graphical user interface (GUI).

Those of skill in the art will appreciate that adjustments to the array geometry can be made. i.e., sensor dimensions and sensor spacing. Vibrational energy 110 includes shear wave energy propagation with shear wavelengths on the order of several tens of millimeters, e.g. approximately 40 millimeters at 200 cycles per second and approximately 20 millimeters at 500 cycles per second.

FIG. 1A contains a representation of the mitral valve that is significant as a source of vibration 146 induced by blood flow through the valve leaflet orifice. The proximity of the mitral valve 146 to the coronary artery 102 and the simultaneous flow of blood through the artery and the valve requires a careful process of combined localization and spectrum classification in the analysis as described in prior patents and pending patent application—U.S. Pat. Nos. 5,617,869, 6,178,344, 6,519,862, 8,419,651, 8,961,427, 9,591,972 and U.S. patent application Ser. No. 16/055,086. U.S. patent application Ser. No. 16/055,086 is hereby incorporated by reference.

Figure 1B:
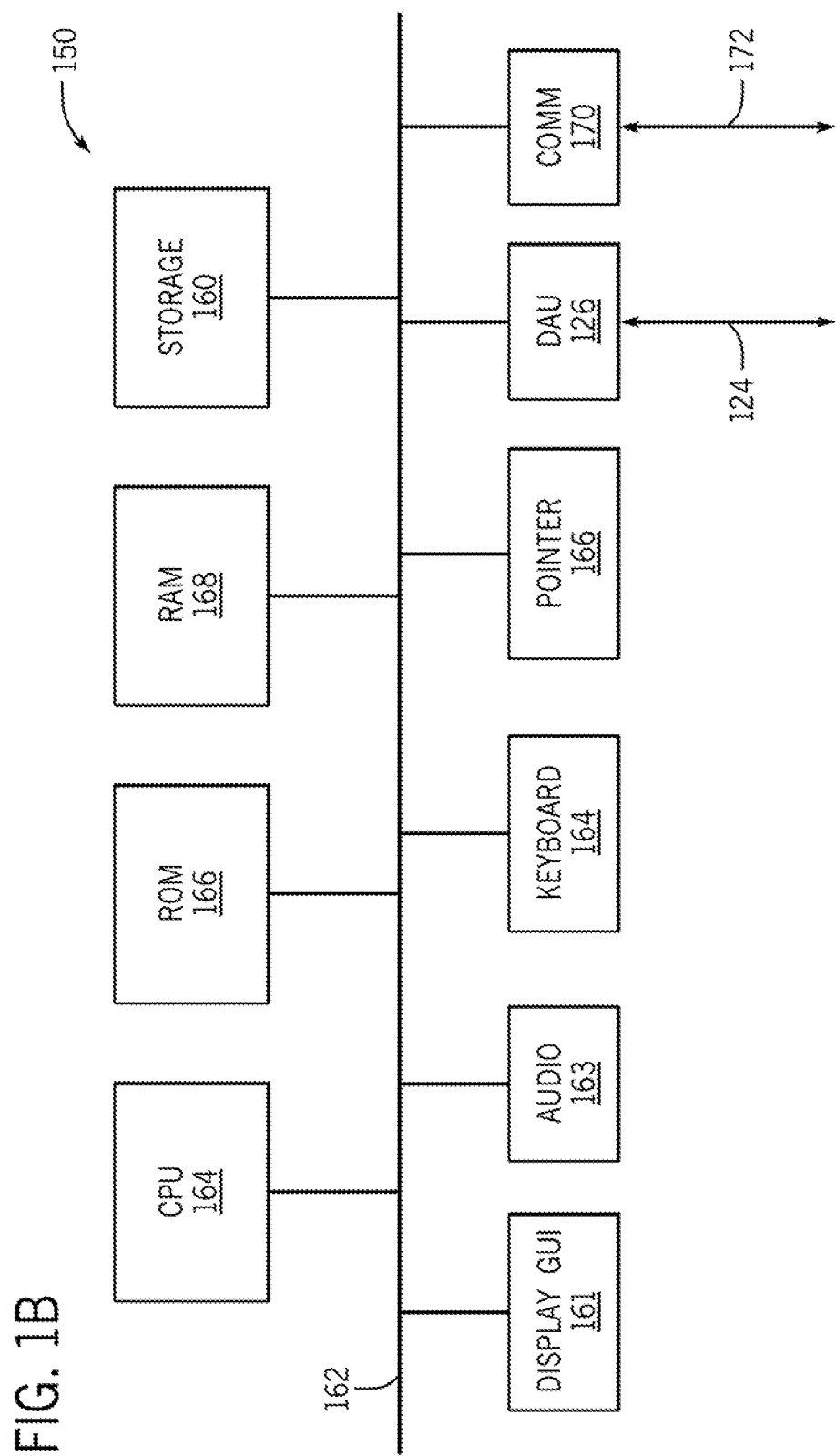
FIG. 1B illustrates a block diagram of a computer system (data acquisition system) in which embodiments of the invention may be used.

FIG. 1B illustrates, generally at 150, a block diagram of a computer system (data acquisition system) in which embodiments of the invention may be used. The block diagram is a high-level conceptual representation and may be implemented in a variety of ways and by various architectures. With reference to FIG. 1B, a data bus system 162 interconnects a Central Processing Unit (CPU) 164. Read Only Memory (ROM) 166, Random Access Memory (RAM) 168, storage 160, a GUI display 161, audio 163, keyboard 164, pointer 166, data acquisition unit (DAU) 126, and communications 170. The bus system at 162 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (FireWire), Universal Serial Bus (USB), or a dedicated bus designed for a custom application, etc. The CPU 164 may be a single, multiple, or even a distributed computing resource. Storage 160 may be Compact Disc (CD), Digital Versatile Disk (DVD), hard disks (HD), optical disks, tape, flash, memory sticks, video recorders, etc. The computer system 150 can be used to receive vibrational cardiac data via 124 from the array 116 of vibration sensors (FIG. 1A). Note that depending upon the actual implementation of a computer system, the computer system may include some, all, more, or a rearrangement of components in the block diagram.

Thus, in various embodiments, vibrational cardiac data is received at 124 for processing by the computer system 150. Such data can be transmitted via communications interface 170 for further processing and diagnosis in a remote location, as illustrated in FIG. 1B at 172. Connection with a network, such as an intranet or the Internet is obtained via 172, as is recognized by those of skill in the art, which enables the data processing device 150 to communicate with other data processing devices in remote locations.

For example, embodiments of the invention can be implemented on a computer system 150 configured as a desktop computer or work station, on for example a WINDOWS® compatible computer running operating systems such as WINDOWS® XP Home or WINDOWS® XP Professional, WINDOWS® 10, Linux, etc. as well as computers from APPLE COMPUTER, Inc. running operating systems such as OS X, etc. Alternatively, or in conjunction with such an implementation, embodiments of the invention can be configured with devices such as parallel computing devices, speakers, earphones, video monitors, etc. configured for use with a Bluetooth communication channel.

Figure 2:
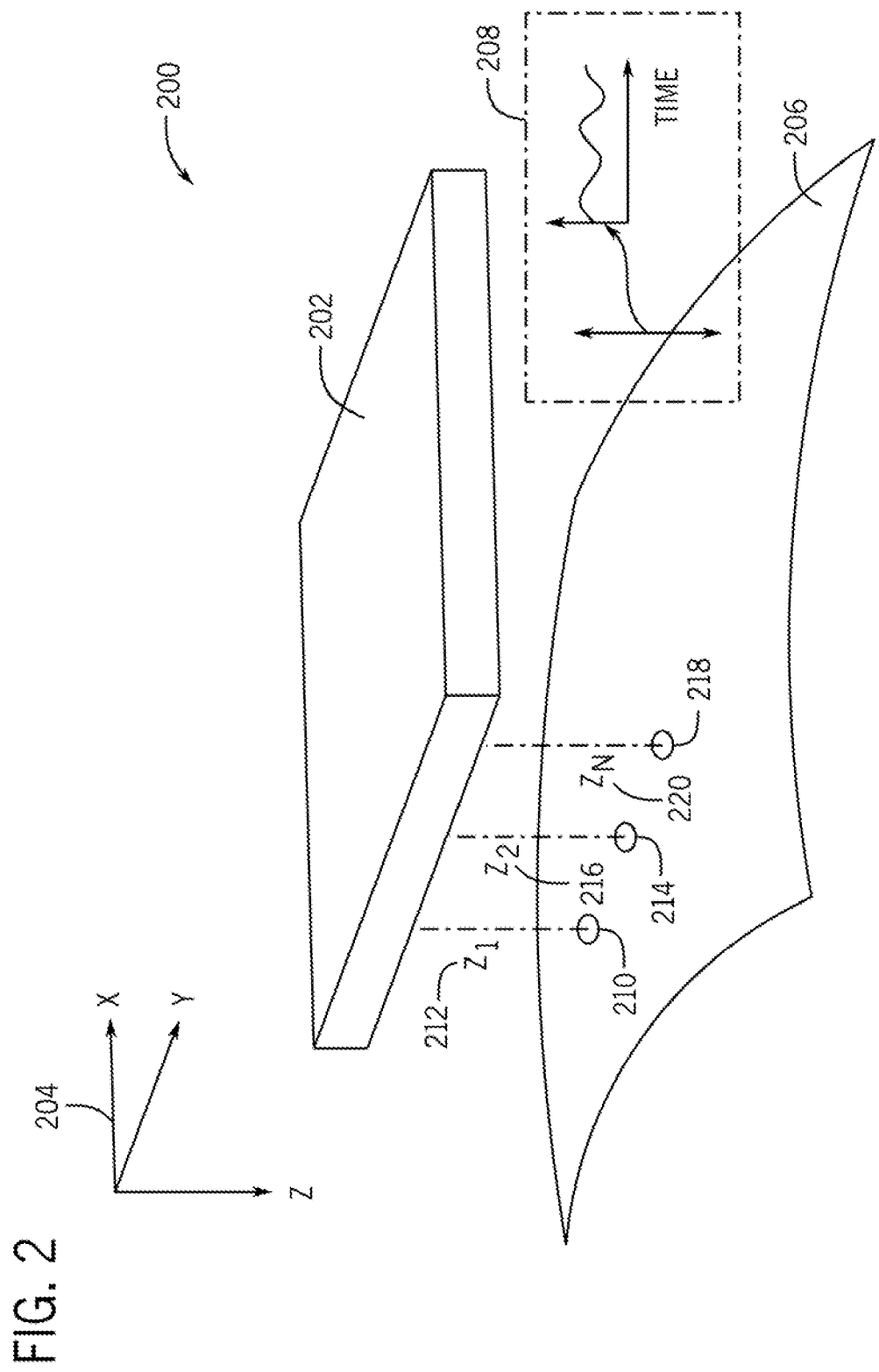
FIG. 2 illustrates measuring body motion at a plurality of locations, according embodiments of the invention.

As described above, the vibrational cardiac data results from measuring the vibration of the surface of a human's body, such as for example the chest (thorax). The terms "vibration," "chest vibration," "motion," "chest motion," "body vibration," "body motion," "thorax vibration," and the like will be used synonymously throughout this description of embodiments. No limitation is implied by the use of one term over the other terms. FIG. 2 illustrates, generally at 200, measuring body motion at a plurality of locations, according to embodiments of the invention. With reference to FIG. 2, a reference plane structure 202 and a measurement datum indicated by axes 204 provide a measurement system with which measurement locations on a human's body surface 206 are referenced. The measurement datum 204 can be separate from the reference plane structure 202 or the measurement datum 204 can be part of the reference plane structure 202. The reference plane structure 202 contains several sensors that measure motion on the surface 206 of a human's body. For example, a first sensor (not shown) is configured to measure motion of a location 210 on the surface 206. The surface 206 is in a state of vibration as indicated at 208 from the excitation previously described in conjunction with FIG. 1A. In the example of FIG. 2, and with no limitation implied thereby, the location 210 is established with an $X_1$, and $Y_1$ value of the first sensor using the reference plane structure 202 and the measurement datum 204. A distance or height of the first sensor relative to the surface 206 is obtained as $Z_1$ at 212. Together, the $X_1$, $Y_1$, and $Z_1$ values for the first sensor define the location 210 on the surface 206 where measurements of surface vibration are made by the first sensor.

Similarly, a location 214 is established with an $X_2$, and $Y_2$ value of the second sensor (not shown) using the reference plane structure 202 and the measurement datum 204. A height of the second sensor relative to the surface 206 is obtained as $Z_2$ at 216. Together, the $X_2$, $Y_2$, and $Z_2$ values for the second sensor define the location 214 on the surface 206 where measurements of surface vibration are made by the second sensor. In various embodiments, a number of sensors in an array is expressed as a general number N. Lastly, a height of the N sensor relative to the surface 206 is obtained as $Z_N$ at 220. Together, the $X_N$, $Y_N$, and $Z_N$ values for the second sensor define the location 218 on the surface 206 where measurements of surface vibration are made by the N sensor. Thus, the unique locations in a three-dimensional space are ascertained using the sensors, the reference plane structure, and the measurement datum. Note that only the $Z_1$, $Z_2$, $Z_N$ distances are illustrated and the $X_1$, $Y_1$, $X_2$, $Y_2$, and $X_N$, $Y_N$ distances have not been illustrated to preserve clarity in the illustration.

Those of skill in the art will appreciate that an orientation of a sensor relative to the measurement datum 204 is also used to determine the locations 210, 214, and 218. For example, if a sensor is mounted in the reference plane structure with its sensing axis parallel to the Z axis of the measurement datum 204 then no X, Y correction is needed. Because in such a case the X, Y values obtained from the sensor's position relative to the measurement datum 204 is sufficient to describe the X and Y coordinate values for sensor on the surface 206. In an alternative embodiment, when a sensor's Z axis is titled at an angle(s) relative to the Z axis, of the measurement datum, then the X and Y values corresponding to the sensor on the surface 206 will need to be corrected using the tilt angle(s) for the sensor.

In operation, the reference plane structure 202 is positioned in space relative to the surface 206. In various embodiments, the reference plane structure can be configured with supports (not shown) such that the reference plane structure rests on the surface 206 and is stabilized thereon, with for example, a body yoke or similar device. In other embodiments, the reference plane structure is supported independently from the surface 206. Thus, in various embodiments, the array is positioned relative to the body such that each sensor has a location, and the location is described by coordinates.

Figure 3:
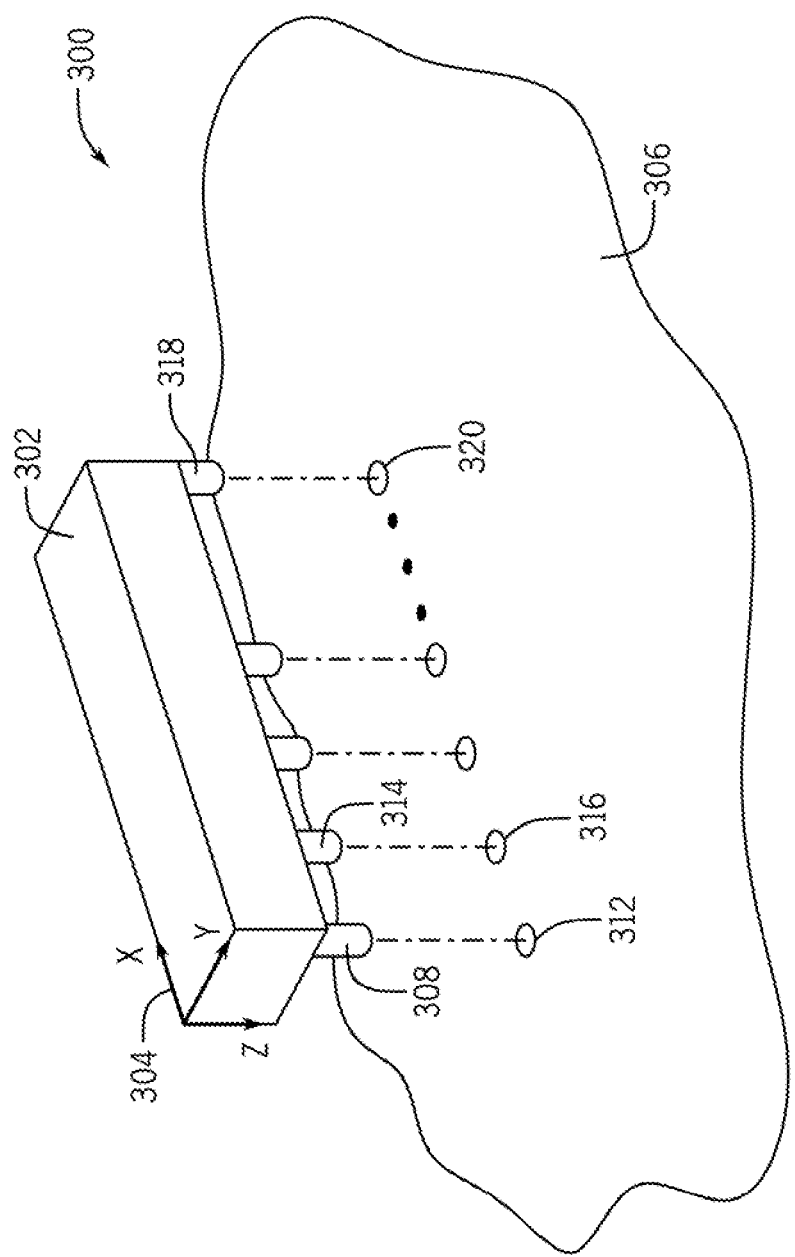
FIG. 3 illustrates measuring body motion with non-contact sensors, according to embodiments of the invention.

FIG. 3 illustrates, generally at 300, measuring body motion with non-contact sensors, according to embodiments of the invention. With reference to FIG. 3, a reference plane structure is shown at 302. A measurement datum is shown at 304. The reference plane structure 302 is configured with a plurality of sensors indicated by general number N at 318. The plurality of N sensors is used to form an array of sensors that is articulated over the surface geometry of the human's body, thereby measuring motion of a human's body indicated at 306. As used in this description of embodiments, "articulate" is used to refer to either a virtual articulation of non-contact sensors (whereby in the case of laser-based sensors, the optical path lengths of the sensors are permitted to be different from each other) as well as a mechanical articulation with contact sensors as described below. Articulate is understood to mean that the sensors articulate (either individually or in groups) to conform to a surface of the body and when they do so, the sensors move in a known and repeatable relationship to each other. A first sensor of the plurality is indicated at 308. The first sensor 308 measures both a distance from the reference plane structure 302 to a first location 312 and motion at the first location 312 on the human's body 306. A second sensor of the plurality is indicated at 314. The second sensor 314 measures both a distance from the reference plane structure 302 to a second location 316 and motion at the second location 316 on the human's body 306. The $N^{th}$ sensor of the plurality is indicated at 318. The $N^{th}$ sensor 318 measures both a distance from the reference plane structure 302 to an $N^{th}$ location 320 and motion at the $N^{th}$ location 320 on the human's body 306. In one or more embodiments the sensors 308, 314 through 318 are optical sensors utilizing a beam of light such as a laser beam. Some examples, of non-contact optical sensors suitable for application herein are, but are not limited to, laser sensors from either Keyence such as the CL-3000 series or the Michelson interferometer series from Picoscale (www.picoscale.com). Note that while non-contact sensors are described herein using laser beams, other physical phenomena are the basis of other non-contact sensors, such as ultrasound, radio frequency energy transmission, other electromagnetic energy-based sensors. In some embodiments, two non-contact sensors are used for each location on the human's body. A first sensor is used to measure a Z coordinate corresponding to the location on the human's body. A second sensor is used to measure the dynamic motion of the surface at the location on the human's body.

Incorporation of sensors 308, 314, through 318 into the reference plane structure 302 is done using the measurement datum 304 thereby providing X, Y coordinate information for each sensor. The Z distance from the measurement datum 304 to the surface 306 establishes the X, Y, Z coordinates for each of the locations 312, 316, through 320 on the human's body 306. Alignment of each sensor relative to the measurement datum 304 establishes any correction angle(s) with respect to the XZ and YZ planes. Such correction angles, if any, together with a Z distance for each sensor permit X, Y, Z location coordinates to be established for each of the measurement locations 312, 316, through 320. The X, Y, Z location coordinates for each of the locations 312, 316, through 320 are used during the beamforming process applied to the vibrational cardiac data resulting from the measurements made of the vibration of the human's body 306.

Figure 4:
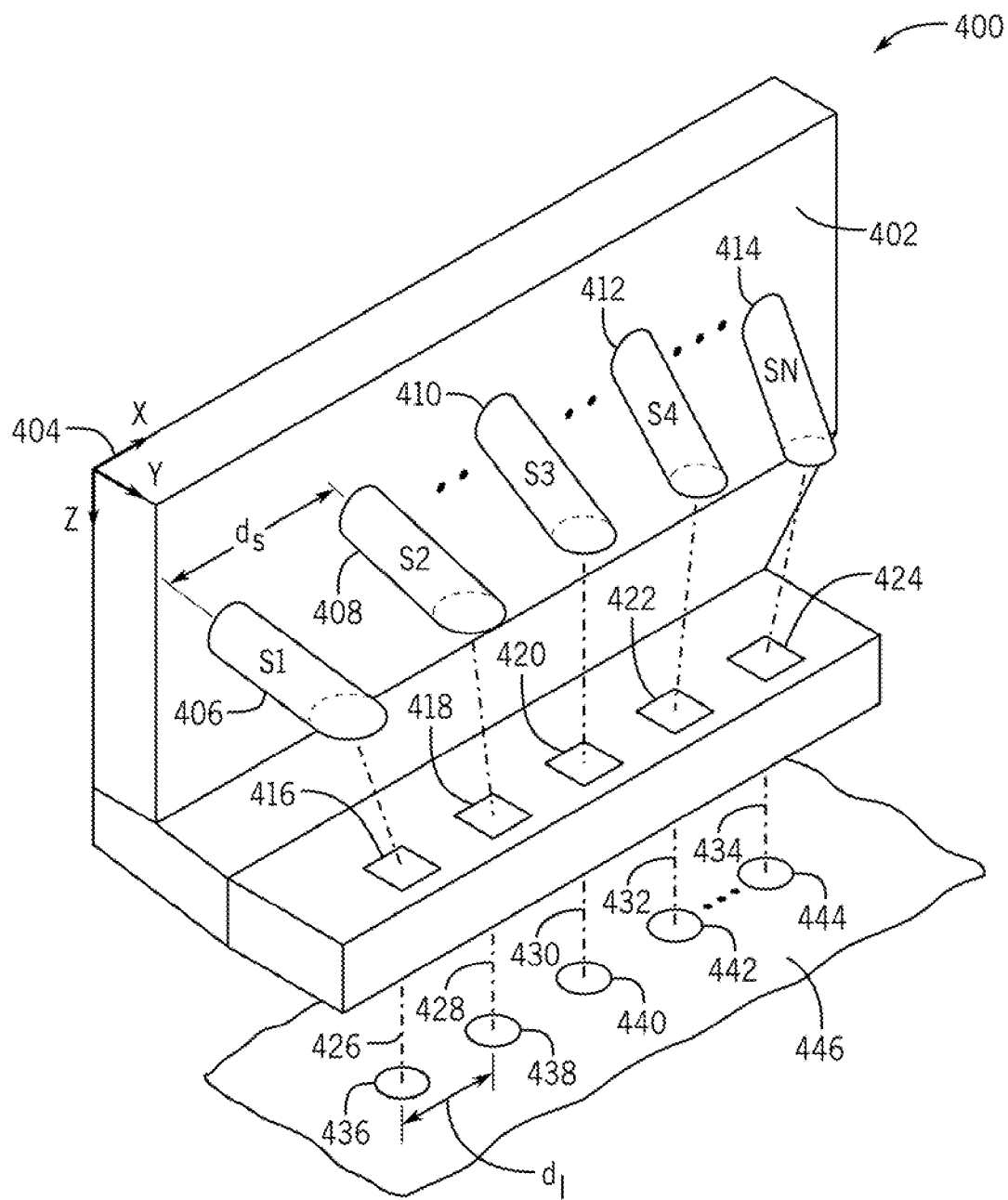
FIG. 4 illustrates measuring body motion with lasers, according to embodiments of the invention.

FIG. 4 illustrates, generally at 400, measuring body motion with lasers, according to embodiments of the invention. In some embodiments, because of the physical dimensions of individual sensors, it is necessary to space apart the individual sensors on the reference frame structure 402 at a spacing that is larger than the separation between measurement locations on the human's body 446. For example, $d_s > d_l$ referring to FIG. 4.

With reference to FIG. 4, a reference plane structure 402 establishes a measurement datum 404. A plurality of N sensors is fixed to the reference plane structure 402 and is indicated by 406, 408, 410, 412, through 414. The sensors are spaced apart nominally at a distance $d_s$. In one or more embodiments, the sensors 406, 408, 410, 412, through 414 utilize laser interferometer beams to measure both distance from the reference frame structure to measurement locations 436, 438, 440, 442, through 444 (e.g., Z distances illustrated in FIG. 2, i.e., 212, 216, and 220) and motion (e.g., 208 in FIG. 2) of the human's body 446 at the measurement locations 436, 438, 440, 442, through 444. Optical elements 416, 418, 420, 422, through 424 are used to set the spacing of measurement locations on the surface of the human's body 446, where the spacing is nominally indicated by $d_l$. Note that generally $d_l$ is a uniform distance between adjacent measurement locations (e.g., 436, 438, 440, 442, and 444) on the surface 446. However, the distance between adjacent measurement locations can be changed by adjustment of one or more of the optical elements 416, 418, 420, 422, and 424.

In various embodiments the optical element are mirrors which change a direction of a beam of light emitted from a sensor. For example, a first sensor 406 ($S_1$) emits a beam of light that reflects off optical element 416 as 426 and is directed to the surface 446 at the location 436. A second sensor 408 ($S_2$) emits a beam of light that reflects off optical element 418 as 418 and is directed to the surface 446 at the location 438. A third sensor 410 ($S_3$) emits a beam of light that reflects off optical element 420 as 430 and is directed to the surface 446 at the location 440. A fourth sensor 412 ($S_4$) emits a beam of light that reflects off optical element 422 as 432 and is directed to the surface 446 at the location 442. A fifth sensor 414 ($S_5$) emits a beam of light that reflects off optical element 424 as 434 and is directed to the surface 446 at the location 444. Separation distance between measurement locations 436, 438, 440, 442, and 444 can be the same or different by adjusting an orientation of optical elements 416, 418, 420, 422, and 424 relative to a sensor's respective incident beam of light. Note that when optical sensors are used in a system, in some embodiments, a single optical sensor is used to measure both motion of the body surface at a measurement location and a distance from the measurement location to the measurement datum. In other embodiments, separate sensors are utilized to measure motion of the body surface at the measurement location and the distance from the measurement location to the measurement datum.

Figure 5:
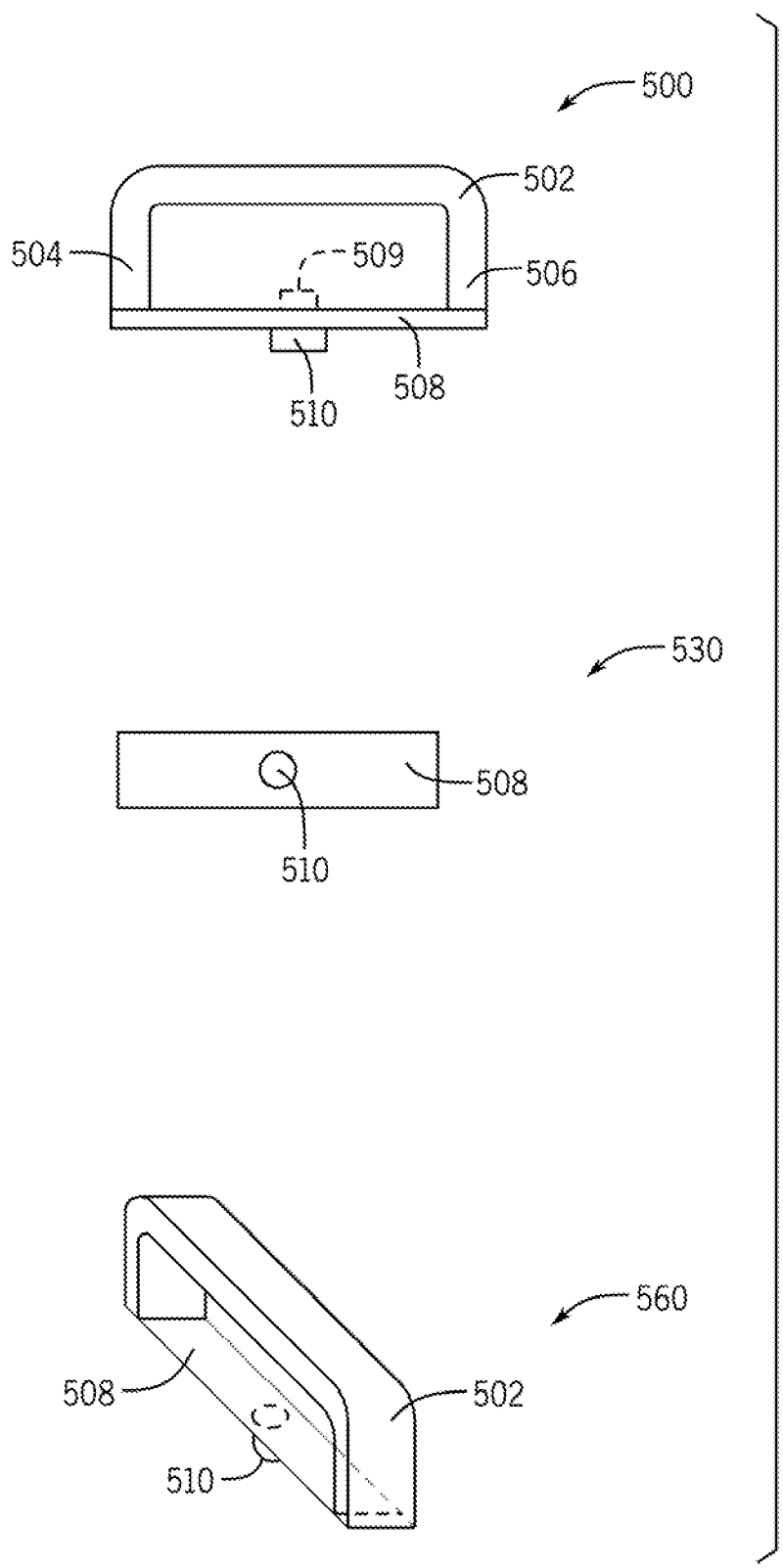
FIG. 5 illustrates a fixture supporting a film sensor, according to embodiments of the invention.

FIG. 5 illustrates, generally at 500, a fixture supporting a flexible film sensor, according to embodiments of the invention. With reference to FIG. 5, such a film sensor is used to perform a contact measurement of the motion of a human's body, such as for example the human's body 206 at measurement locations 210, 214, through 218. With reference to FIG. 5 at 500, a fixture 502 has a first end 504 and a second end 506. Disposed between the first end 504 and the second end 506 is a film sensor 508. The film sensor has a contact pad 510. The contact pad makes contact with a human's body and imparts surface motion (vibration) to the film sensor, thereby causing the film to vibrate in a direction perpendicular to the plane of the film.

A bottom view of the film sensor is presented in 530 and a top perspective view is presented in 560. In various embodiments, the film sensor is made from a film using piezoelectric polyvinylidene difluoride (PVDF). Each side of the PVDF film is covered with a thin layer of a conductive material such as silver paint or the like. Electrical leads are connected to the respective sides to provide a ground and a signal lead for connection to one or more stages of amplification before processing in, for example, a beamforming algorithm. Note that in some embodiments, the film sensor 508 is configured with an optional sensor 509. In some embodiments, the optional sensor 509 is an accelerometer, velocimeter, or the like, configured to measure vibration in a direction substantially normal to a plane of the film sensor 508. In such embodiments, employing the optional sensor 509, the film sensor 508 functions as a mounting surface for the optional sensor 509.

In various embodiments, the fixture 502 is made from an elastic material, such as a metal, a plastic, etc. It is desirable to place the PVDF film sensor under a tensile preload. The tensile preload can be imparted during assembly by compressing the U shape of the fixture 502. During compressing the first end 504 and the second end 506 are moved toward each other. The film sensor 508 is attached to each of the ends 504/506. When compression of the ends 504/506 is released or reduced, the elasticity of the fixture 502 provides the desired tensile preload to the film sensor 508. Thus, the film sensor 508 is self-tensioned by the fixture 502 during the assembly process.

Figure 6:
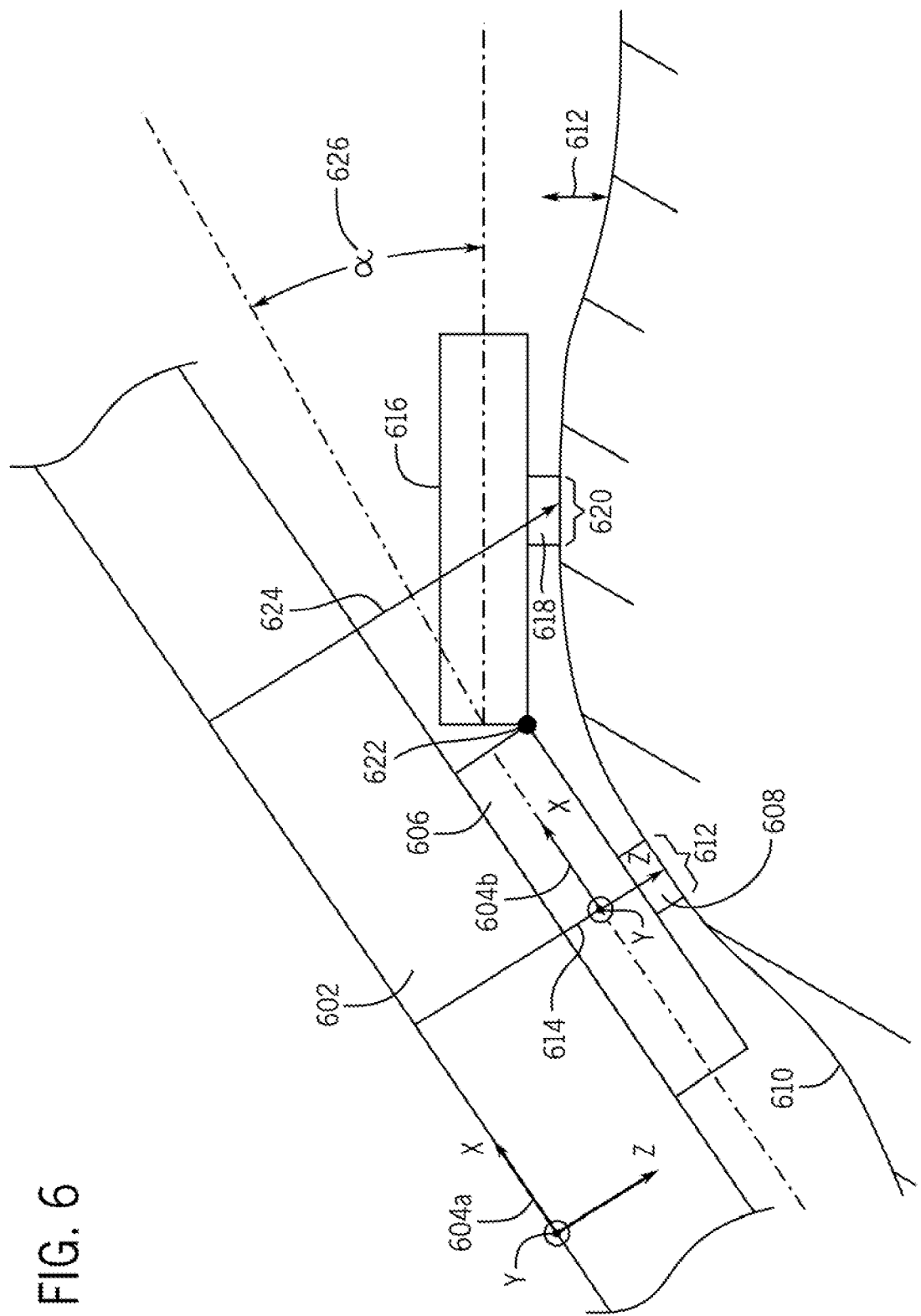
FIG. 6 utilizing multiple fixtures, according to embodiments of the invention.

FIG. 6 illustrates, generally at 600, utilizing multiple fixtures, according to embodiments of the invention. With reference to FIG. 6, a reference plane structure 602 establishes a measurement datum 604a. A first fixture supports a first sensor as indicated at 606. The first sensor has a contact pad 608 that is in contact with a surface 610 of a human's body. A vibration field exists over the human's body surface as is indicated at 612. The sensor and contact pad 606/608 are responsive to motion of the body surface 610 at a first measurement location 612. Note that in some embodiments, the reference plane structure 602 is a part of the first fixture, as indicated by location of an optional measurement datum 604b on the first fixture/sensor 606. Thus, the reference plane structure is optional. Note that a measurement datum can be in a variety of places, such as but not limited to, those shown at 604a and 604b.

Spatial coordinates $X_1$, $Y_1$, $Z_1$ corresponding to the first measurement location 612 relative to the measurement datum 604a are provided by dimensions of 606/608 and the reference plane structure 602. Thus, a $Z_1$ distance 614 of the first location 612 to the measurement datum 604a is obtained thereby.

A second fixture supports a second sensor as indicated at 616. The second sensor has a contact pad 618 that is in contact with a surface 610 of a human's body. The second sensor and contact pad 616/618 are responsive to motion of the body surface 610 at a second measurement location 620. The second fixture 616 articulates relative to the first fixture 606 as indicated at 622. Articulation of adjacent fixtures permits the sensor pads 608 and 618 to conform to a curvature of the human's body as illustrated in FIG. 6. Articulation at 622 is accomplished in various embodiments through a hinge connection. A hinge connection is accomplished in various embodiments with a mechanical hinge, e.g., a pin, a ball and socket, a layer of flexible material such as a fabric, a flexible plastic layer, etc. In some of the figures described below, embodiments of articulation at 622 are illustrated with hinges mounted to the feet of adjacent Omega shaped fixtures. Note that articulation is described herein both between individual sensors as well as between assemblies of sensors. Thus, in some embodiments, one sensor can articulate relative to another. Or a first group of sensors can articulate relative to an adjacent second group of sensors. Alternatively, a single sensor can be configured to articulate relative to a group of sensors. Described below, in some of the figures that follow and with no limitation implied thereby, is articulation between adjacent groups of five sensors.

Spatial coordinates $X_2$, $Y_2$, $Z_2$ corresponding to the second measurement location 620 relative to the measurement datum 604a are provided by dimensions of 616/618 and the reference plane structure 602. Thus, a $Z_2$ distance 624 of the second measurement location 620 relative to the measurement datum 604a is obtained thereby. In various embodiments, the principles embodied in FIG. 6 are extendable to a plurality of sensors and a plurality of fixtures to provide conformable arrays having a general number of fixtures and a general number of sensors as needed to obtain the vibrational cardiac data. Various embodiments are created to accommodate multiple sensors in a fixture as well as multiple fixtures rotatably coupled together.

Figure 7A:
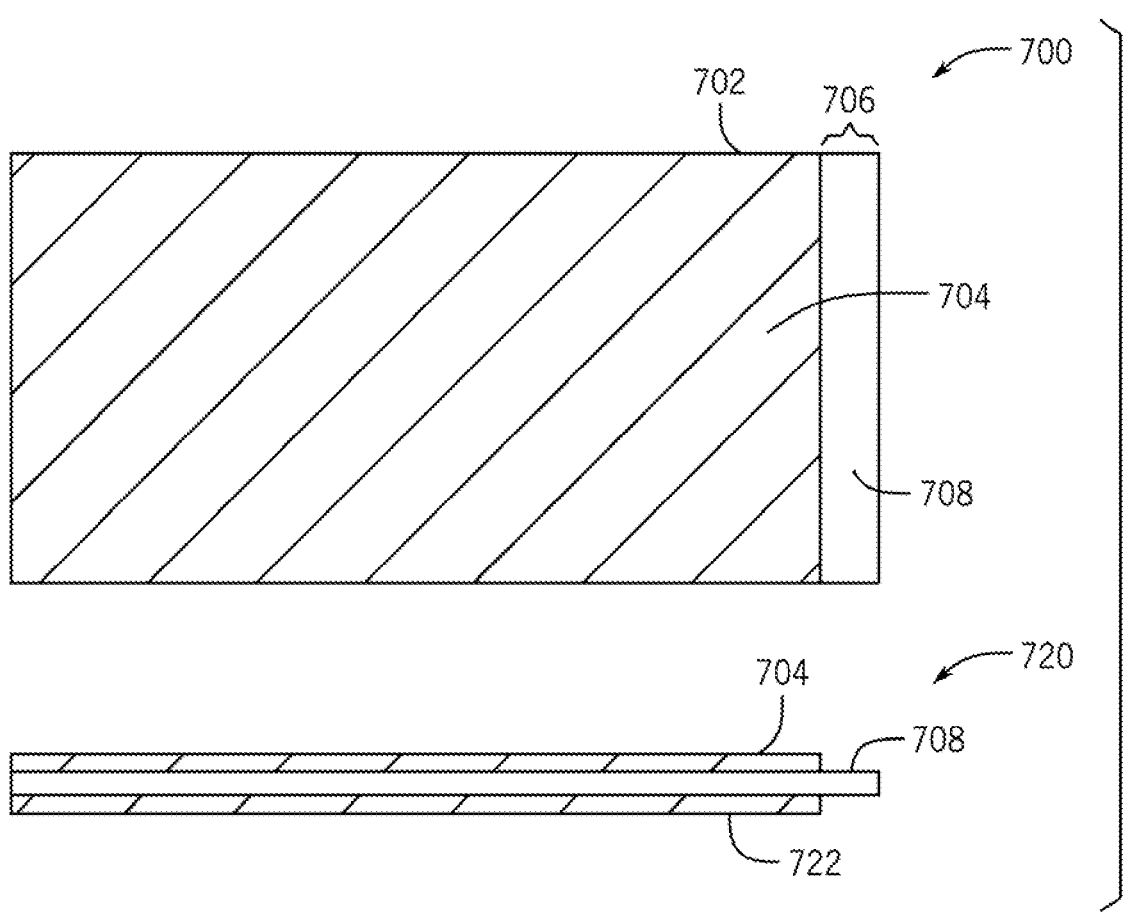
FIG. 7A illustrates a top view of a film used to make a multi-sensor array, according to embodiments of the invention.

FIG. 7A illustrates, generally at 700, a top view of a film used to make a multi-sensor array, according to embodiments of the invention. View 720 illustrates a corresponding side view. The following discussion refers collectively to the top and side view. With reference to FIG. 7A, a PVDF film is illustrated at 702. The PVDF film 702 has a first conductive layer disposed thereon at 722 (ground layer) and a second conducive layer 704 (signal layer). When the PVDF film 702 is placed in a state of strain, for example when excited by the vibration of a surface of a human's body as previously described, a voltage is generated between the two conductive layers 722 and 704. In various embodiments the conducive layers are made from silver paint. In other embodiments, gold paint is used to form the conductive layers. Those of skill in the art will recognize that sensors can be fashioned from PVDF film in various ways. The methods described herein are given by way of example and do not limit embodiments of the invention.

Figure 7B:
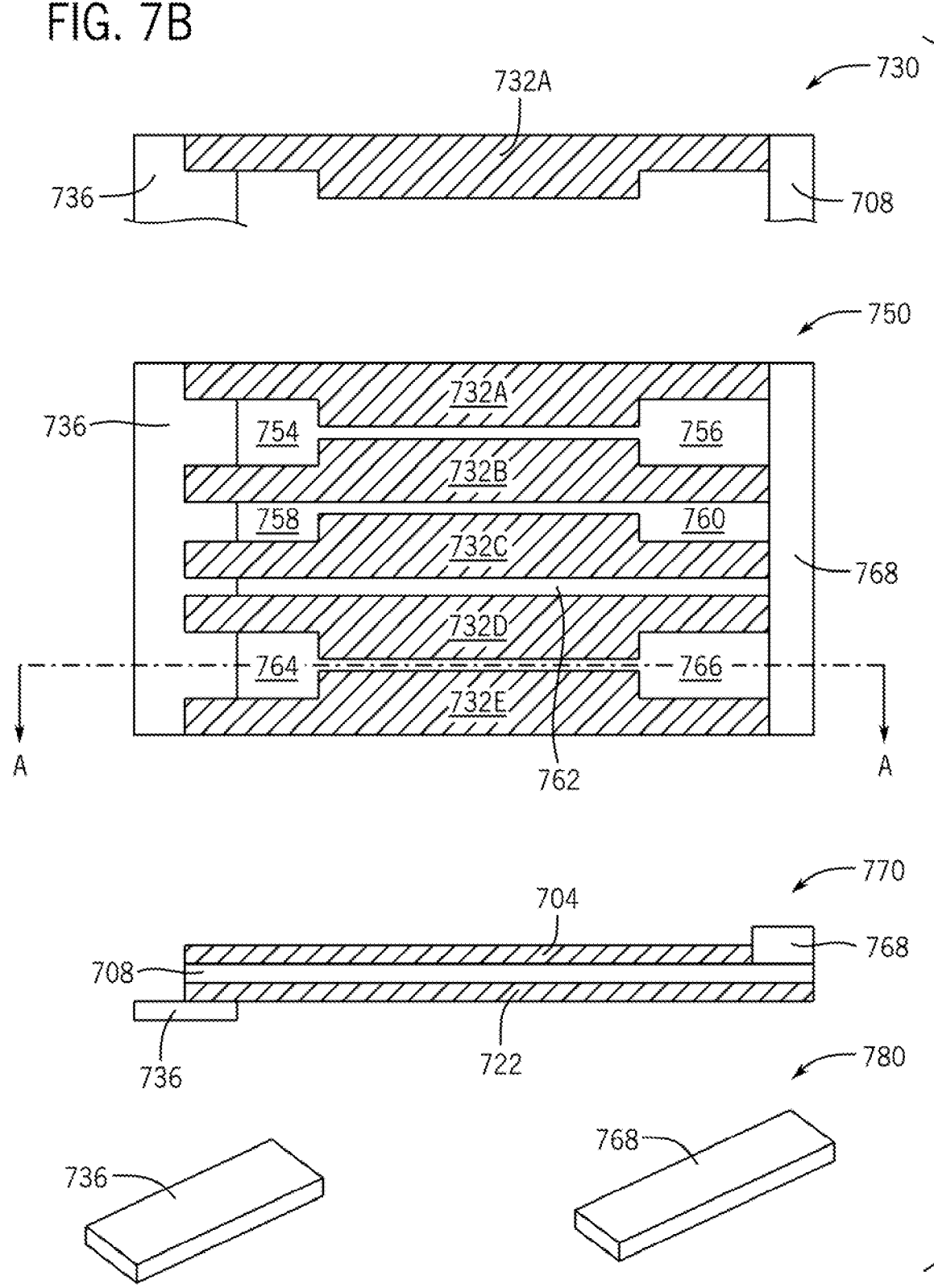
FIG. 7B illustrates processing the PVDF film 702 into an array of five sensors, according to embodiments of the invention.

Accordingly, in one or more embodiments, the conductive layers 704 and 722 are deposited on the PVDF film 708 such that a region 706 remains free of conductive layers. FIG. 7B illustrates processing the PVDF film 702 into an array of five sensors. Five sensors are selected by way of example and do not limit embodiments of the invention. Accordingly, in some embodiments more than five sensors are created and yet in other embodiments less than five sensors are created from a piece of PVDF film.

View 730 illustrates a sensor shape 732A. The sensor shape 732A is established by cutting away material from the sheet 702 leaving the shape shown in view 730. Cutting portions of PVDF sheet 702 can be facilitated by fixing a reinforcing strip of nonconductive material, such as plastic 736 along a left side of the PVDF film 702 as illustrated. Fixing can be accomplished with glue or with other forms of mechanical fixation.

View 750 depicts a five-element array of sensors. A first sensor is indicated at 732A and a second sensor is indicated at 732B. Portions of the PVDF film 702 have been removed as indicated at 754 and 756 along with the slit therebetween. Removal of material 702 (754/756) permits sensor 732A to move freely relative to sensor 732B. A reinforcing strip of nonconductive material 768 is fixed to the bare PVDF layer 708 along a right side of the PVDF film 702. Reinforcing strips 736 and 768 are generally thicker than the PVDF film thickness. Apply tensioning force to each of the reinforcing strips permits the PVDF film 702 to be more uniformly tensioned in a following step.

Similar removal of PVDF film material is indicated at 758 and 760 along with the slit therebetween, thereby freeing a second sensor 732B from the PVDF film 702. A slit 762 is created by removing PVDF film therefrom. Finally, PVDF film is removed from region 764 and 766 along with the slit therebetween. Thus, a fourth sensor 732D and a fifth sensor 732E are created thereby.

An end view of the five-element array is illustrated at 770. View 780 presents a perspective view of the reinforcing members 736 and 768. Reinforcing members are made from various non-conducting materials such as either fiberglass, PLA plastic which is convenient for use in a 3D printer, or a metal coated with insulation material.

Many different arrangements of sensor film are possible. For example, FIG. 7C illustrates another arrangement of the multi-sensor PVDF film array described above in FIG. 7B, according to embodiments of the invention. Referring to FIG. 7C, view 730 illustrates a sensor shape 732A. The sensor shape 732A is established by cutting away material from the sheet 702 leaving the shape shown in view 730. Cutting portions of PVDF sheet 702 can be facilitated by fixing a reinforcing strip of nonconductive material, such as plastic 736 along a left side of the PVDF film 702 as illustrated. Fixing can be accomplished with glue or with other forms of mechanical fixation.

View 750 depicts a five-element array of sensors. A first sensor is indicated at 732A and a second sensor is indicated at 732B. Portions of the PVDF film 702 have been removed as indicated at 754, 764, 756 and 766 along with the slit 762 therebetween the sensor configurations 732. Removal of material 702 (754, 764, 756 and 766) allows the entire film assembly to slide uniformly into alignment on the fastener during assembly and to then be secured by the fasteners (e.g., 848 and 812 as shown in FIG. 8A below) when alignment is achieved. A reinforcing strip of nonconductive material 768 is fixed to the bare PVDF layer 708 along a right side of the PVDF film 702. Reinforcing strips 736 and 768 are generally thicker than the PVDF film thickness and accept application of a tensioning force to each of the reinforcing strips which permits the PVDF film 702 to be more uniformly tensioned in a following step.

Removal, cutting, scissoring, slotting, and etching of PVDF film material is indicated at 754, 764, 756 and 766 and 760 for mechanical fastener insertion in addition to the slit therebetween 762, thereby freeing a second sensor 7323 from the PVDF film 702. A slit 762 is created by removing the entirety of the PVDF film therefrom. Finally, PVDF film is removed from region 764 and 766 along with the slit therebetween. Thus, a fourth sensor 732D and a fifth sensor 732E are created thereby.

A side view of the five-element array is illustrated at 770. View 780 presents a perspective view of the reinforcing members 736 and 768. Reinforcing members are made from various non-conducting materials such as either fiberglass, PLA plastic, which is convenient for use in a 3D printer, or a metal coated with an insulation material.

FIG. 8A illustrates, generally at 800, film sensor clamping, according to embodiments of the invention. With reference to FIG. 8A, section A-A from view 750 (FIG. 7B) is illustrated at 800 in cross-section. As noted above, the conductive layer 722 functions as the sensor's electrical ground (GRND) and in the cross-section A-A the conductive layer 732l) provides the signal for the individual sensor that was created from the conductive layer 702. It is desirable to mount the PVDF film in such a fashion that all of the PVDF sensors experience a state of approximate uniform tension. In order to place the PVDF film in tension the PVDF film is clamped at opposing ends.

A lower clamp bar 804 and an upper clamp bar 806 capture a first side of the PVDF film and the reinforcing member 768. A conductive strip 802 is applied to the lower clamp bar 804. In various embodiments, the conductive strip 802 is a layer of copper tape that adheres to the lower clamp bar 804. In other embodiments a thin sheet of conductive material is used for conductive strip 802. The conductive strip 802 provides electrical contact with the conductive ground plane layer 722 of the PVDF film thereby providing a terminal strip for bringing the electrical ground (GRND) of the sensor out to the rest of the system (e.g., preamplifier stage, etc.).

During pre-assembly, the upper clamp bar 806 is placed on a top side of the first side of the PVDF film. A stiffening bar 808 is placed on a top side of the upper clamp bar 806. Holes 810 and 816 are provided through the lower clamp bar 804, the upper clamp bar 806, and the stiffening bar 808. During the PVDF film pre-assembly step a bolt 812 passes through the hole 810. Washer and nut 814 together with the bolt 812 provide a means for the application of clamping force that clamps the first end of the PVDF film sheet. The hole 816, washer and nut 820, and a vernier bolt 818 are used to secure the PVDF film assembly to a fixture and to provide fine tension adjustment at a corner of the PVDF film assembly all of which are described more completely below.

Similar to the first side, at an opposing second side of the PVDF film, a lower clamp bar 834 and an upper clamp bar 836 capture the second side of the PVDF film. A conductive strip 852 is applied to the upper clamp bar 836 in strips that align with the upper conductive layers e.g., 732A, 732B, 732C, 732D, and 732E of the PVDF film that were fashioned from conductive layer 704, thereby providing signal lead connection from the individual sensors (FIG. 7B). In various embodiments, the conductive strips 852 are made from a layer of copper tape that adheres to the upper clamp bar 836, which can also be made from a printed circuit board. In other embodiments, a thin sheet of conductive material is used for conductive strips 852. The conductive strips 852 provide electrical contact with the conductive layers 732A, 732B, 732C, 732D, and 732E of the PVDF film sensors thereby providing a terminal strip for bringing the electrical signal lines from the sensor out to the rest of the system (e.g., preamplifier stage, etc.).

During pre-assembly of 800, prior to mounting in an articulating fixture, the upper clamp bar 836 is placed on a top side of the second side of the PVDF film. A stiffening bar 838 is placed on a top side of the upper clamp bar 836. Holes 840 and 846 are provided through the lower clamp bar 834, the upper clamp bar 836, and the stiffening bar 838. During the PVDF film pre-assembly step a bolt 848 passes through the hole 846. Washer and nut 850 together with the bolt 848 provide a means for the application of clamping force that clamps the second end of the PVDF film sheet. The hole 840, washer and nut 844, and a vernier bolt 842 are used to secure the PVDF film assembly to a fixture and to provide fine tension adjustment at a corner of the PVDF film assembly all of which are described more completely below.

Figure 8B:
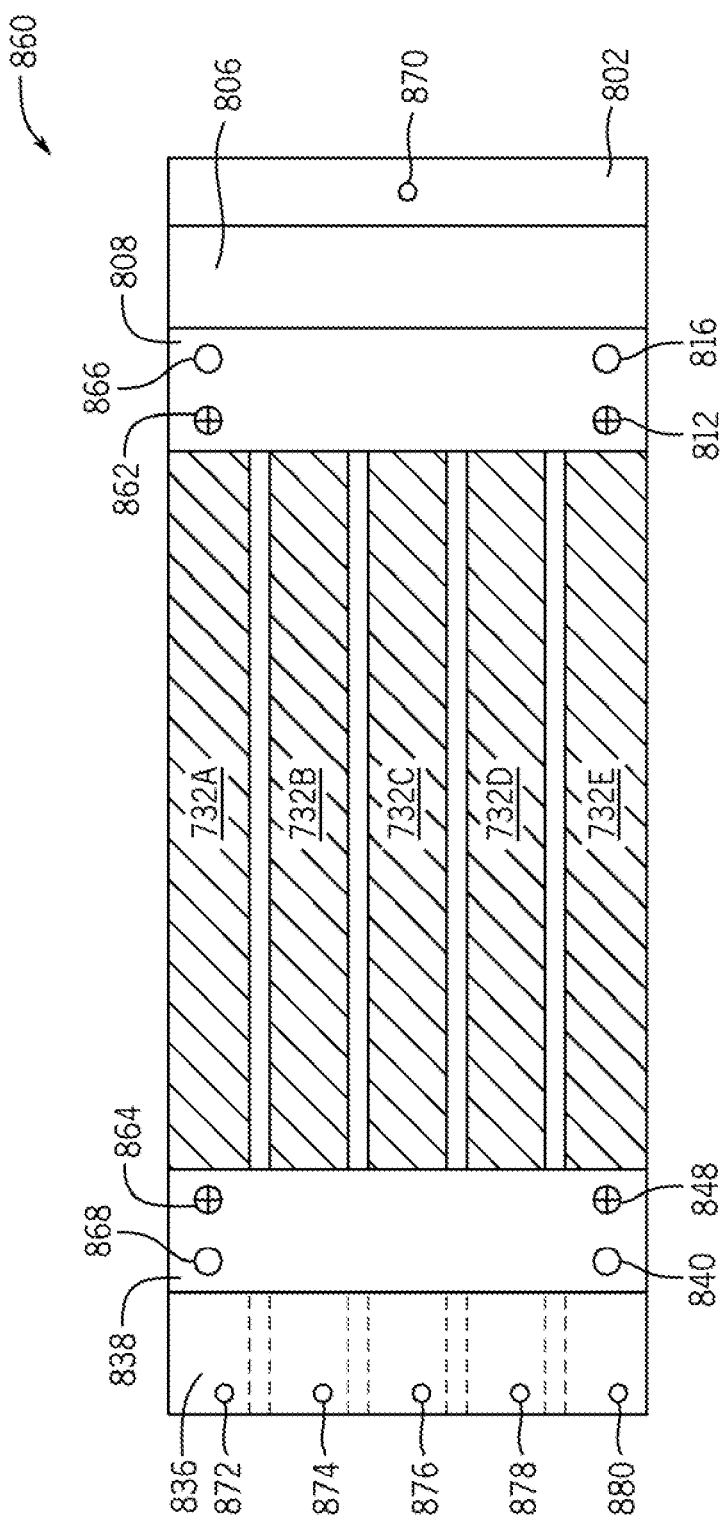
FIG. 8B illustrates pre-assembly of a multi-sensor film array, according to embodiments of the invention.

FIG. 8B illustrates, generally at 860, pre-assembly of a multi-sensor PVDF film array, according to embodiments of the invention. With reference to FIG. 8B, the pre-assembled multi-sensor film array from FIG. 8A is shown in top view. The pre-assembly described in FIG. 8A for the bolt 812, holes 810, and washer and nut 814 is repeated at the opposite end the lower clamp bar 804, upper clamp bar 806 and stiffening bar 808 and is represented in FIG. 8B as 862. Similarly, the pre-assembly described in FIG. 8A for the bolt 848, hole 846, and washer and nut 850 is repeated at the opposite end the lower clamp bar 834, upper clamp bar 836 and stiffening bar 838 and is represented in FIG. 8B as 864.

An electrical connection to ground is provided by hole 870 through 802/804. Individual electrical connections to the signals from the individual sensors are provided by holes 872, 874, 876, 878, and 880. Holes 872 through 880 pass through 836/852.

Figure 8C:
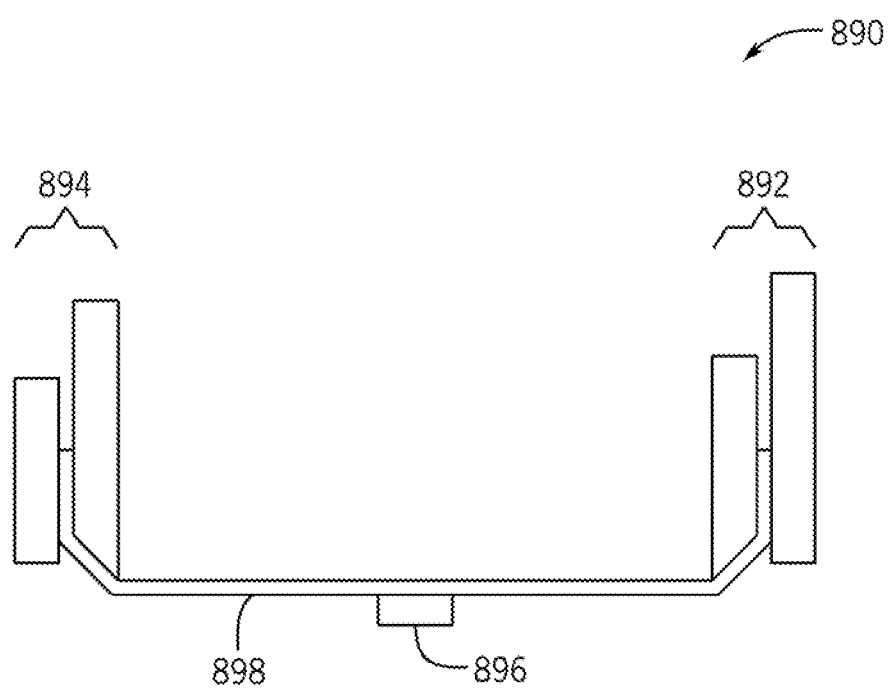
FIG. 8C illustrates a pre-assembled configuration of a multi-sensor film array, according to embodiments of the invention.

FIG. 8C, illustrates a pre-assembled configuration of the multi-sensor film array, according to embodiments of the invention. In the preassembled state, the PVDF film array is handled at the first side 892 and second side 894 by means of the clamping bars. Assembly proceeds by rotating each of the two clamped sides approximately ninety (90) degrees relative to the plane of the sensors to form a U shape as shown in FIG. 8C at 890. The layers of the PVDF film have been previously described in detail in the figures above. However, in FIG. 8C the PVDF film is represented simply by 898 where the individual layers are not depicted in order to preserve clarity in the illustration. A contact pad (for contact with a surface of a human) is mounted to each sensor in the array. A contact pad on one sensor of the array is indicated at 896.

Figure 9:
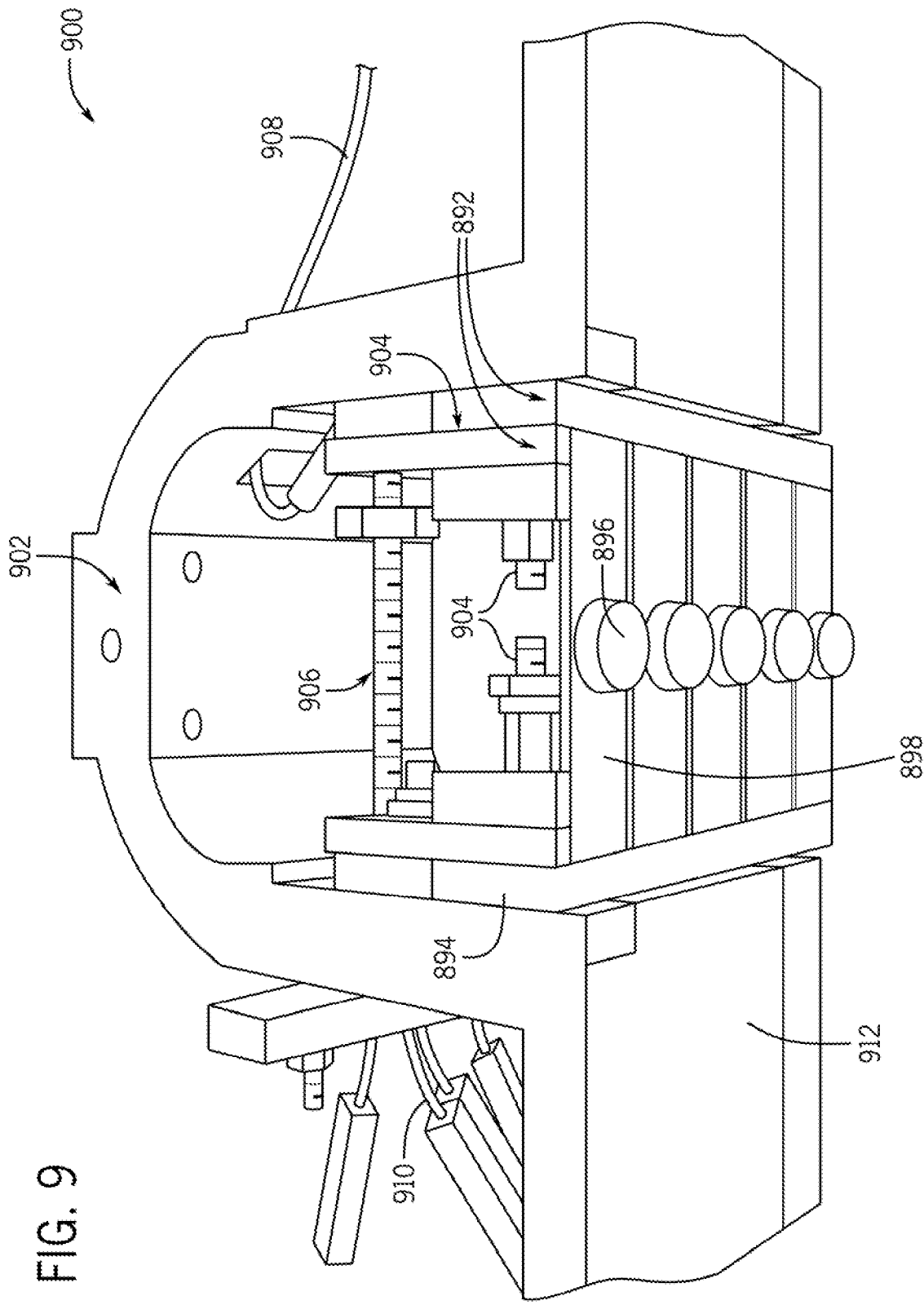
FIG. 9 illustrates, generally at 900, a lower perspective view of a multi-sensor fixture, according to embodiments of the invention.

FIG. 9 illustrates, generally at 900, a lower perspective view of a multi-sensor fixture, according to embodiments of the invention. With reference to FIG. 9, a fixture 902 is provided from an elastic material in a U shape that is configured to receive the preassembled PVDF film array from view 890. Note that the U shape illustrated in the figures herein is similar to a shape of a Greek letter known as "Omega." In various embodiments, different shapes are used with no limitation implied thereby. For example, a circular shape, a square shape, a rectangular shape, etc. can all be used to provide an elastic structure to support the PVDF film sensors. Reference herein to the shape of the fixture 902 using term "Omega" does not imply any limitation, the term is used merely for convenience. The elastic material used for the Omega fixture 902 can be used to provide tensile preload to the PVDF film. The U-shaped arch of the Omega fixture 902 can be either compressed or expanded with the tensioning bolt 906 to allow tension adjustment of the preassembled PVDF film array that has been inserted into the opening of the mouth of the U-shape. The elasticity of the fixture 902 can be used to impart a tensile preload to the preassembled PVDF film array. This is accomplished by manipulating the Omega fixture 902 with the fixture tensioning bolt 906. For example, in one embodiment, the fixture tensioning bolt 906 compresses the ends of the Omega fixture 902 drawing the ends closer together. Next, the preassembled PVDF film array is attached to the ends of the Omega fixture 902 while the Omega fixture 902 is compressed. Then, the fixture tensioning bolt 906 is operated to reduce compression of the Omega fixture 902, thereby resulting in application of a tensile preload in the preassembled PVDF film array. As shown in FIG. 9, the preassembled PVDF film array has been inserted into the Omega fixture 902. The first side 892 of the preassembled PVDF film array is fastened to the Omega fixture 902 with two vernier tensioning bolts and nuts 818 and 820 (FIG. 8A) and holes 816 and 866 (FIG. 8B). The vernier tensioning bolts 818 pass through holes (not shown) in the Omega fixture 902.

Similarly, the second side 894 of the preassembled PVDF film array is fasted to the Omega fixture 902 with two vernier tensioning bolts and nuts 842 and 844 (FIG. 8A) and holes 840 and 868 (FIG. 8B). The vernier tensioning bolts 842 pass through holes (not shown) in the fixture 902.

The fixture tensioning bolt 906 passes through the fixture 902 and is adjustable from the outside of the Omega fixture 902 as described herein. Sensor signal leads are indicated at 910 and provide unique signal leads to each of the sensor signal connections, such as for example 872, 874, 876, 878, and 880 (FIG. 8B). An electrical ground lead 908 is illustrated and is connected to 870 (FIG. 8B).

Figure 10:
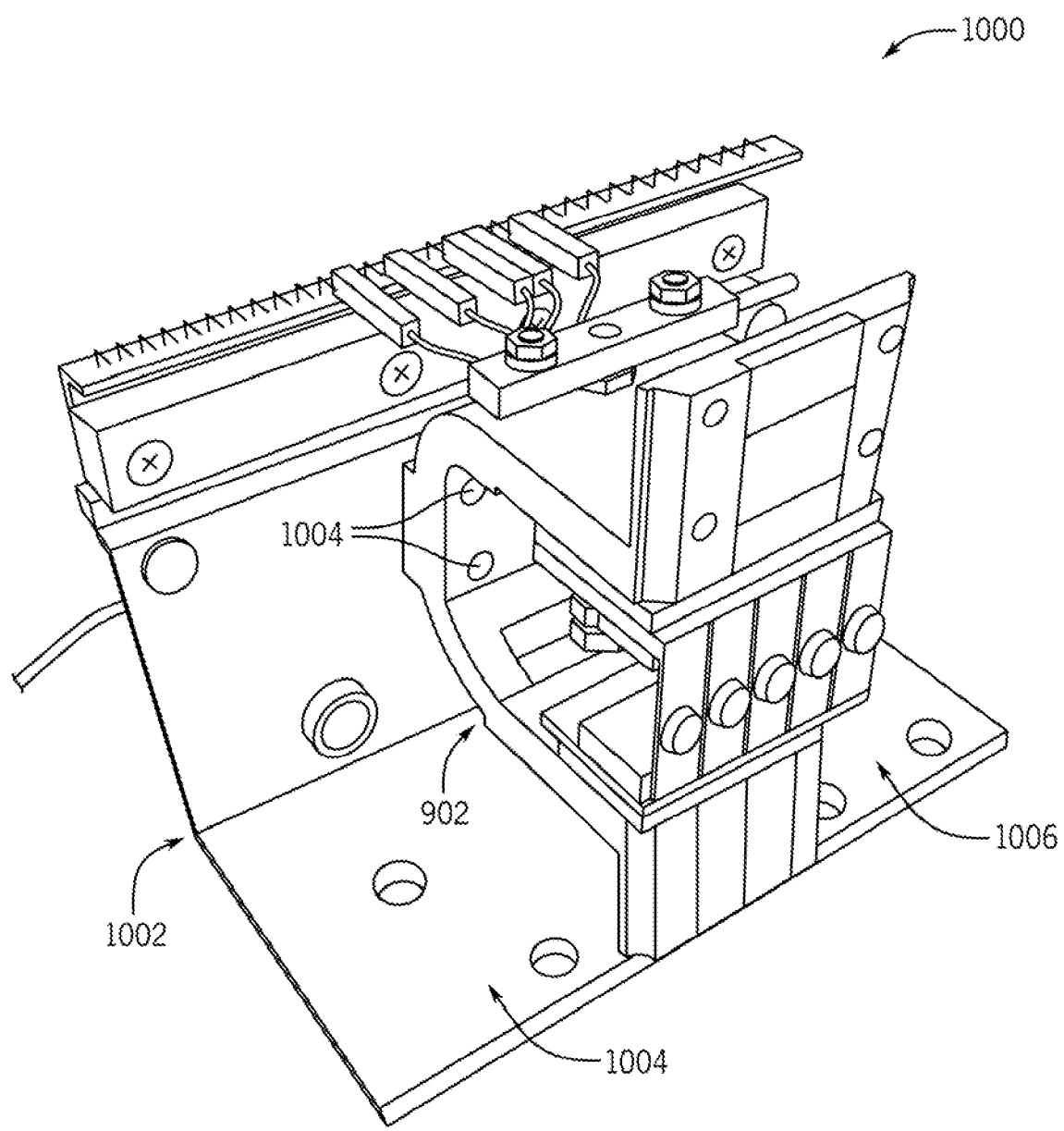
FIG. 10 illustrates another lower perspective view of a multi-sensor fixture, according to embodiments of the invention.

FIG. 10 illustrates, generally at 1000, another lower perspective view of a multi-sensor fixture, according to embodiments of the invention. With reference to FIG. 10, a reference plane structure 1002 is shown with the fixture 902 coupled thereto. The fixture 902 is coupled to the reference plane structure in various ways such as with bolts 1004 as well as with other bolts not shown in the view presented. In the embodiment shown, the reference plane structure 1002 is configured to receive a second fixture at a second fixture location 1004 and a third fixture at a third fixture location 1006. All five sensors and their contact pads are visible in the view presented in FIG. 10 for the first fixture 902.

Figure 11:
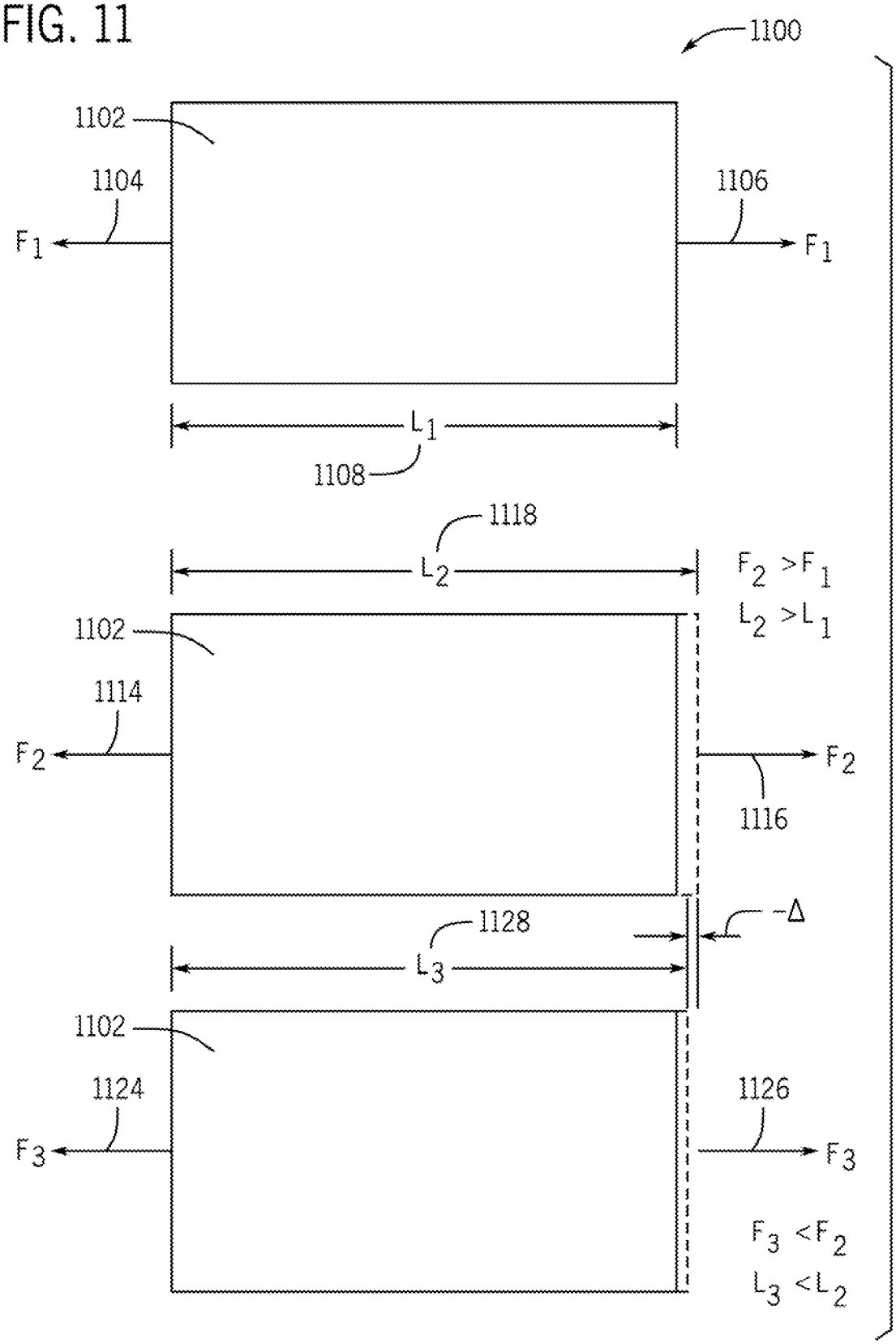
FIG. 11 illustrates tensioning a film sensor, according to embodiments of the invention.

FIG. 11 illustrates, generally at 1100, tensioning a film sensor, according to embodiments of the invention. With respect to FIG. 11, a multi-sensor film is illustrated at 1102. In various embodiments, the multi-sensor film 1102 is representative of 750 (FIG. 7B) or 860 (FIG. 8B), etc. In various embodiments, a fixture tensioning bolt such as 906 (FIG. 9) is used to apply and to adjust a magnitude of a load experienced by the multi-sensor film 1102. The load is applied to the multi-sensor film 1102 by either releasing or increasing the compression in the Omega fixture with a tensioning bolt. An initial length of the multi-sensor film 1102 is indicated at 1108 as $L_1$. $F_1$ indicated by 1104/1106 represents equal and opposite loads applied by a fixture, such as 902 (FIG. 9) to the multi-film sensor 1102. Rotation of the fixture tensioning bolt 906 in one direction spreads (e.g., a counterclockwise direction) the sides of the Omega-shaped fixture 902 thereby increasing a length of the multi-sensor film 1102 from the first length $L_1$ at 1108 to a second length $L_2$ at 1118. Where $L_2 > L_1$. Rotation of the fixture tensioning bolt 906 in a second direction (e.g., a clockwise direction) lowers the applied load to $F_3$ at 1124/126 resulting in a length of $L_3$. Where $L_3 < L_2$. Thus, by rotation of the fixture tensioning bolt 906 the first and second sides of the multi-sensor film 1102 are moved in a substantially parallel fashion relative to each other. This method of adjusting tension in the multi-sensor film 1102 is referred to as coarse tensioning.

Figure 12:
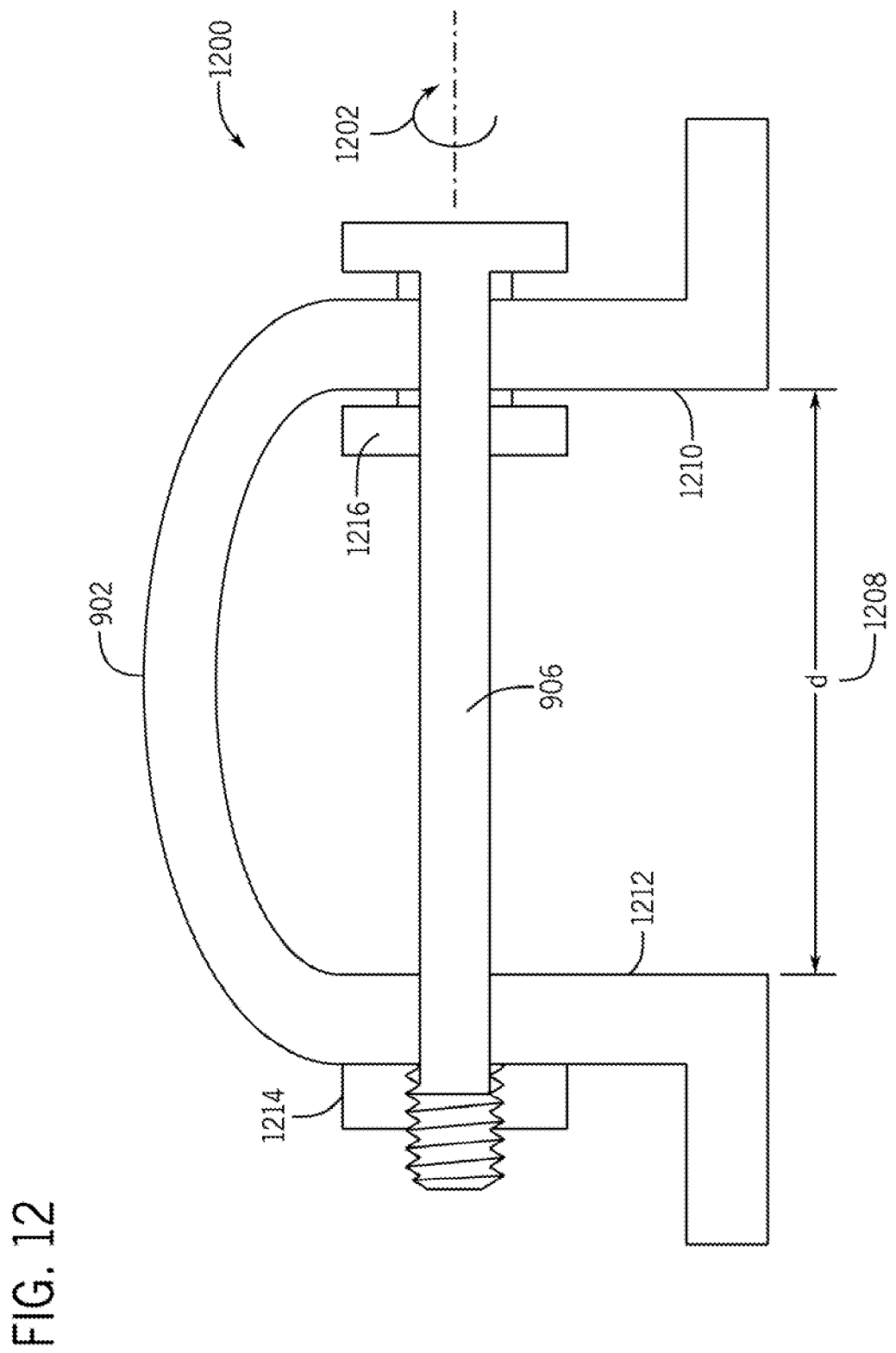
FIG. 12 illustrates adjusting tension in a fixture, according to embodiments of the invention.

FIG. 12 illustrates, generally at 1200, adjusting tension in a fixture, according to embodiments of the invention. With reference to FIG. 12, the fixture 902 is shown with fixture tensioning bolt 906 passing therethrough from a first side 1210 to a second side 1212. Rotation of the fixture tensioning bolt 906 as indicated at 1202 results in a change of separation distance d at 1208 as described above in conjunction with FIG. 11. In the configuration presented, a threaded nut 1214 is fastened to the fixture 902. A bearing surface 1216 is fastened to the fixture tensioning bolt and rotates with the fixture tensioning bolt 906. Configured as shown, clockwise rotation results in a decrease in separation distance d at 1208 and counterclockwise rotation results in an increase in separation distance d at 1208. Note that many variations are possible within the description of embodiments presented herein. The mechanism illustrated is given by way of example and does not limit variations. For example, 1214 can be replaced by a threaded through hole in the fixture 902. In yet other embodiments an external clamp is used to permit adjustment in a separation distanced at 1208.

Figure 13A:
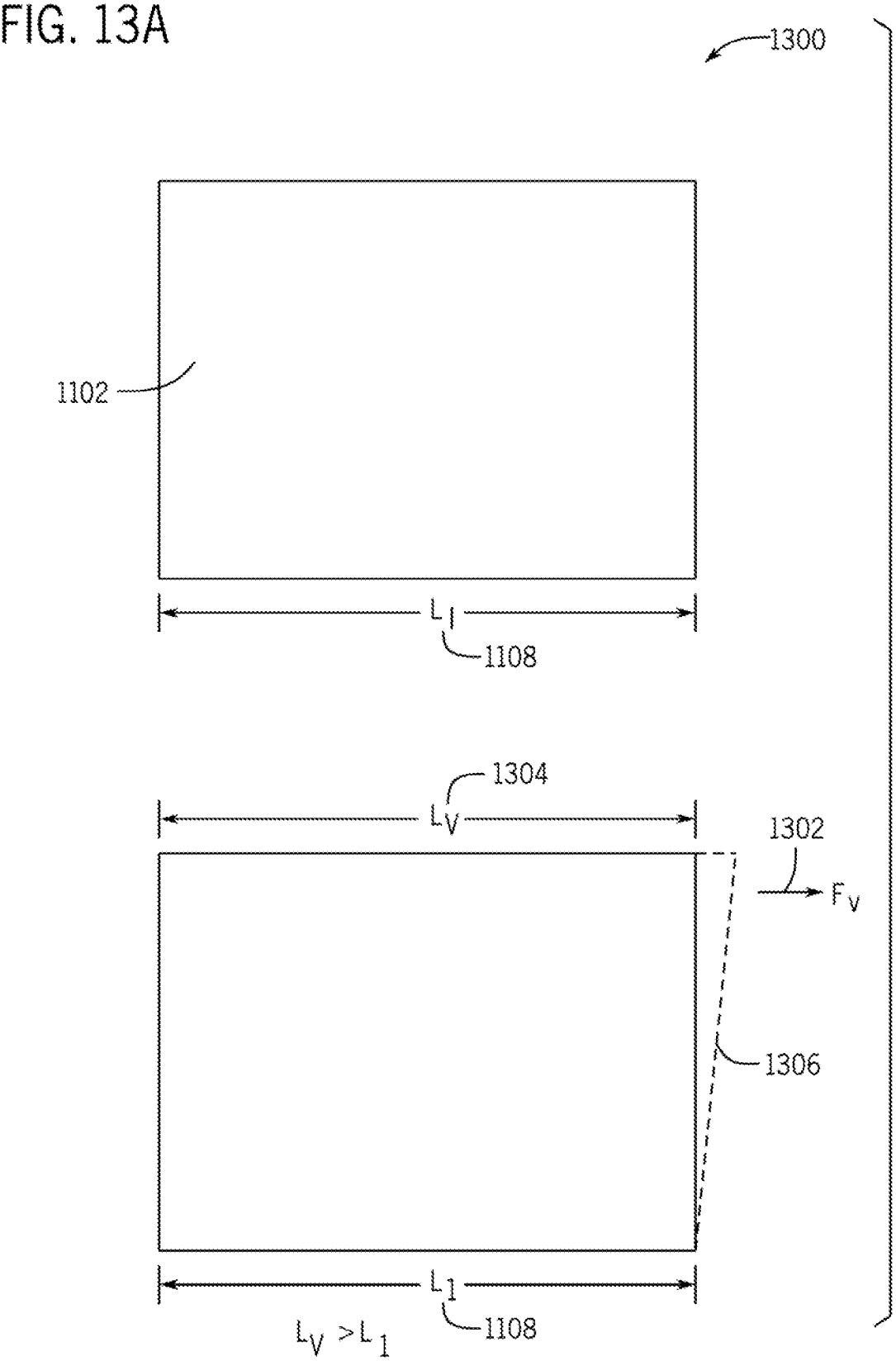
FIG. 13A illustrates vernier tensioning a sensor film, according to embodiments of the invention.

FIG. 13A illustrates, generally at 1300, vernier tensioning a sensor film, according to embodiments of the invention. With reference to FIG. 13A, the multi-sensor film 1102 is illustrated having a length $L_1$ at 1108 and $L_2$ at 1302. Conceptually, the state of strain illustrated in 1102 in FIG. 13A is representative of a given coarse tension adjustment, such as for example a state of strain shown in FIG. 11. Vernier tensioning bolts are provided at approximately each corner of the plane created by the multi-sensor film. Adjustment of one vernier tensioning bolt produces a force and corresponding displacement at the bolt location. The applied load creates a non-parallel loading and resulting non-uniform displacement along a length of the side of the multi-sensor film. Such a deformed state due to vernier tensioning is illustrated qualitatively at 1306. The fixture 902 used to support the multi-sensor film thus provides five (5) different tension adjustment points, i.e., a coarse adjustment producing approximately parallel movement of each opposing side of the sensor plane and independent corner adjustment (vernier adjustment). Together, these five tension adjustment points are used to make the tension experienced by each sensor approximately the same. This uniform tension process contributes to ensuring uniform sensor response to motion at the chest wall of the human.

Figure 13B:
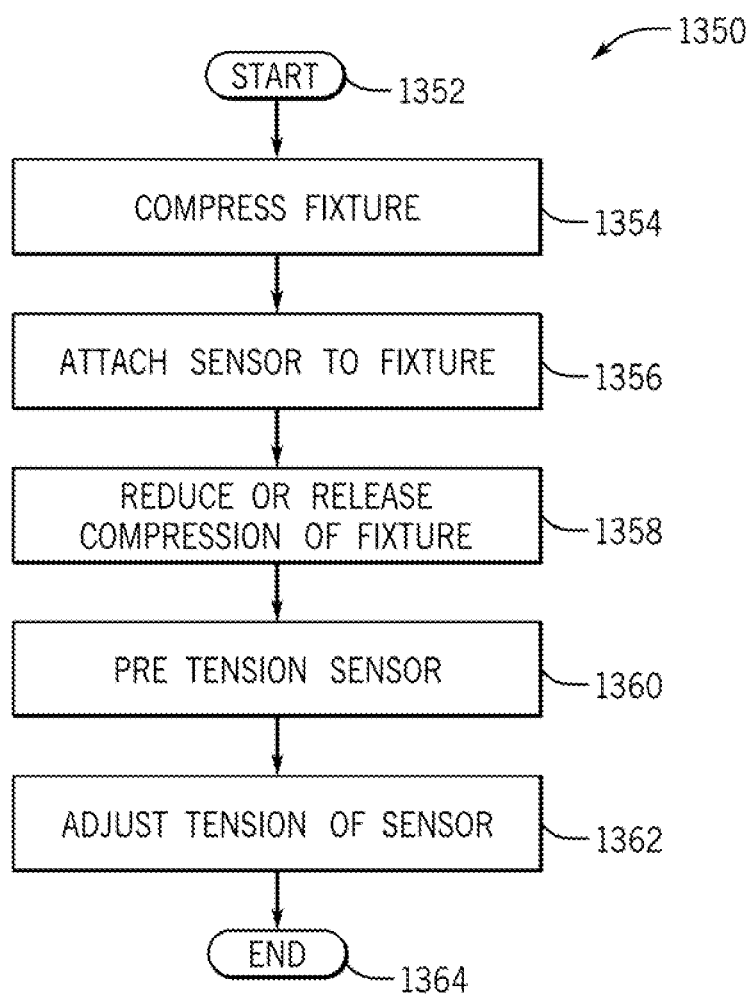
FIG. 13B illustrates a process to tension a film sensor according to embodiments of the invention.

FIG. 13B illustrates, generally at 1350, a process to tension a film sensor according to embodiments of the invention. With reference to FIG. 13B, a process begins at a block 1352. At a block 1354 a fixture is compressed. Examples of compressing a fixture are illustrated above with for example, FIG. 5. FIG. 9, FIG. 10, etc. At a block 1356 a sensor is attached to the fixture. In various embodiments, the sensor is a PVDF film sensor as described above. At a block 1358 compression of the fixture is released or reduced. Reduction of compression is accomplished by reversing the compression provided at the block 1354. At a block 1360 a sensor is tensioned. In various embodiment this is called a state of pre-tension or tensile preload. Optionally, at a block 1362 the state of tension in the sensor is adjusted. A process ends at a block 1364.

Figure 14:
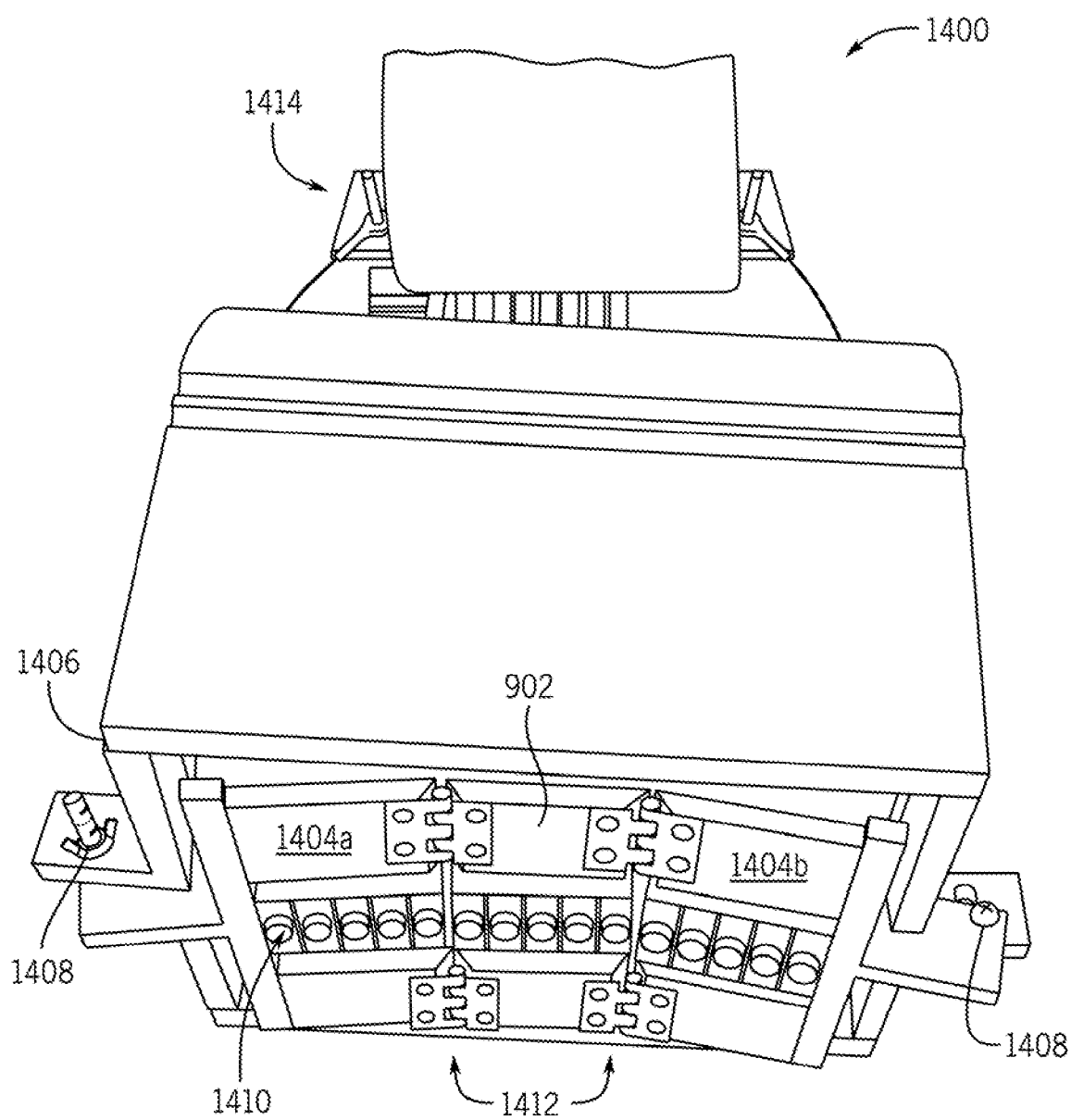
FIG. 14 illustrates a lower perspective view of multiple fixtures, according to embodiments of the invention.
Figure 15:
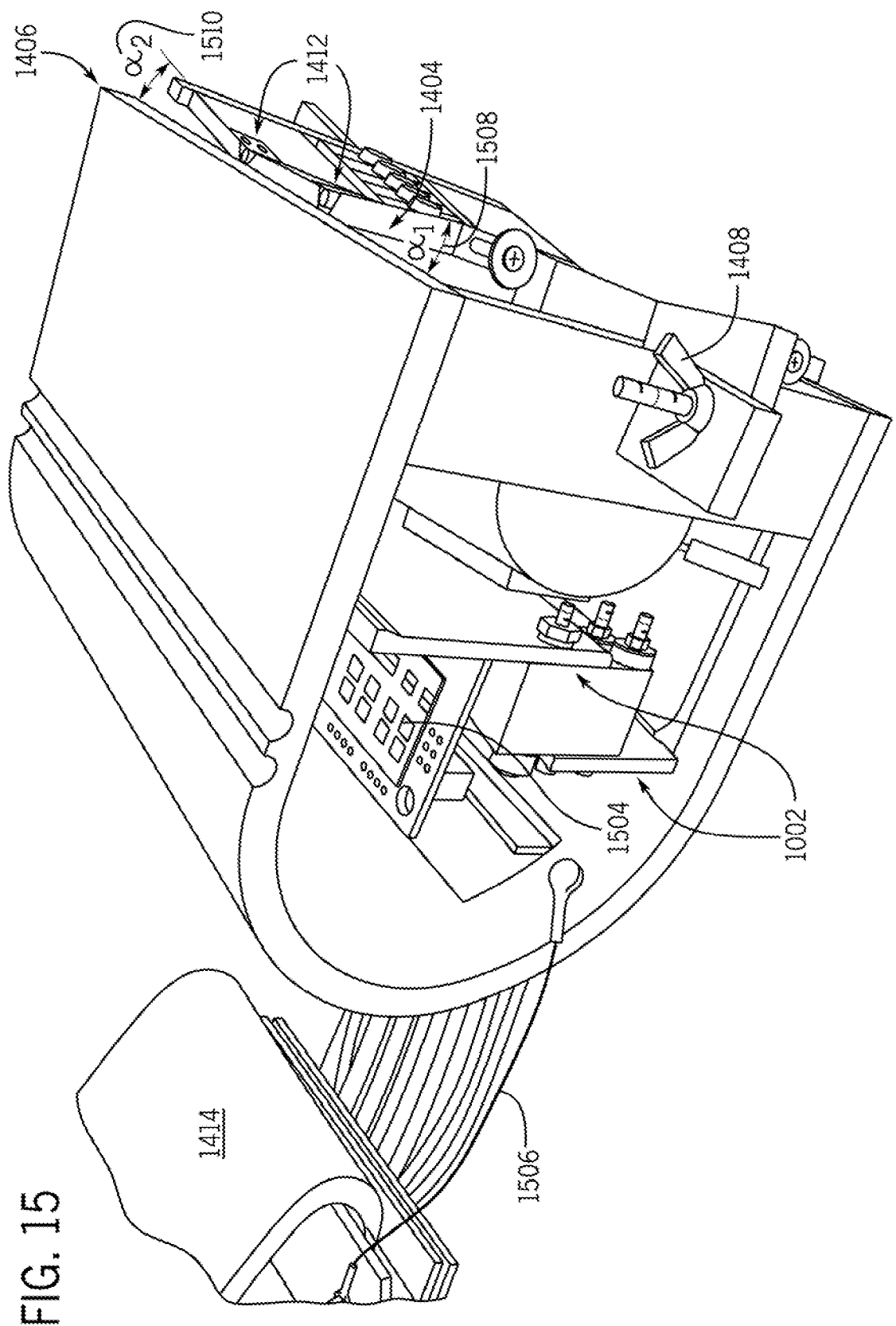
FIG. 15 illustrates an end perspective view of multiple fixtures, according to embodiments of the invention.

FIG. 14 illustrates, generally at 1400, a lower perspective view of multiple fixtures, according to embodiments of the invention. FIG. 15 illustrates an end perspective view of multiple fixtures, according to embodiments of the invention. With reference to FIG. 14 and FIG. 15 collectively, the reference plane structure 1102 (FIG. 10) is attached to a measurement datum 1406. The first fixture 902 is coupled to the reference plane structure 1002 as described above in conjunction with FIG. 10. Rotatably coupled to the first fixture 902 is a second fixture 1404a and a third fixture 1404b. Fixture 1404a and fixture 1404b are rotatably coupled to the first fixture 902 via articulation hinges 1412.

In the case of the embodiment shown in FIG. 14 and FIG. 15, when the fixtures are placed on a human's chest, the fixtures articulate to conform to the curvature of the human's chest and form angles 1508 and 1510 between the planes of the sensors and the measurement datum 1406. Subsequent to fixing the articulation, with a device such as lock bolts 1408, a first articulation angle 1508 is formed between the measurement datum 1406 and the second fixture 1404a. A second articulation angle 1510 is formed between the third fixture 1404b and the measurement datum 1406. The first articulation angle 1508 provides coordinate information for sensors contained within the second fixture 1404a. The second articulation angle 1510 provides coordinate information for sensors contained within the third fixture 1404b. The coordinate information together with the geometry of the fixture and multi-sensor film enable calculation of the measurement location for each sensor in the array of sensors contained within the three fixtures described herein. The geometry of the fixture includes, but is not limited to, center-to-center sensor spacing, distance from a contact pad surface to the measurement datum for the sensors located in the first fixture. The ability to rotate the Omega-fixtures independently at the hinge points and thereby conform the entire assembly of fixtures in a piece-wise linear fashion to the curvature of the body surface is called array aperture articulation. The methodology of combining the Self-Tensioning of the sensor film by the elasticity of the Omega fixture and the Articulating (fixture) Combination of multiple fixtures is referred to herein as STAC.

As described above, with FIG. 14 and FIG. 15, coordinate information is in the form of an angle that a fixture makes with a measurement datum. Alternatively, coordinate information is obtained as linear distance between a point on a fixture and a measurement datum. In some embodiments, one or more optical sensors are used to provide coordinate information on a fixture that is used to mount a contact sensor. Thus, in some embodiments, optical sensors are included with contact sensors to provide coordinates for measurement locations on a human's chest.

Array Position and Determination of Propagation Widow Through Chest Structures

As described above in conjunction with FIG. 1A, it is advantageous to locate the array of sensors over a space between adjacent ribs. The space between adjacent ribs, known as the intercostal space, is referred to herein as an advantageous window for direct propagation from the heart surface to the vibration sensors. It is critical to place the sensor array (whether it be a contact sensor array. e.g., STAC array assembly or non-contact array) with the sensors centered as accurately as possible in the intercostal window to avoid refraction and forward scattering of the propagating wave energy by contiguous ribs. A procedure for proper sensor positioning entails the use of ultrasonic probing for the rib-free depth reading of the thorax beneath the sensors to the surface of the heart. This is accomplished with sparse placement of ultrasonic imaging transmit-receive (TR) transducer units along the axis of the sensor array. In other embodiments to placement, a digital examination (using a human fingertip) is made and a marking procedure is employed to facilitate placement of the array of sensors.

Contact Sensor Array Placement

In various embodiments, with a PVDF multi-film sensor array in operation, a human typically reclines in either a prone or inclined chest-up position. The multi-fixture system 1400 is lowered from above the human's chest until the contact pads of the sensor make contact with the human's chest. In some cases, either a chest wrap and/or a necklace-like yoke 1414 is used to stabilize the multi-fixture system 1400 relative to the human. In one or more embodiments, the articulation bolts 1408 are loosened thereby permitting the first fixture 1404a and third fixture 1404b to rotate relative to the stationary second fixture (central fixture 902). The operator manipulates the first and third fixtures through a range of angles until an optimum position is found for all of the sensors in the array. An optimum position is one in which all of the sensors are in contact with the surface of the human's chest. When the optimum position is found the operator tightens the articulation bolts 1408 to fix the array shape, thereby preserving the curvature established through the step of fitting the array to the curvature of the human's chest. Illustrated herein are three fixtures, where each of the three fixtures contains five (5) independent sensors. Thus, a fifteen (15) element array of arbitrary curvature is described that articulates to conform to the curvature of a human's chest. The system provides coordinates for measurement locations on the human's chest that correspond to the location of vibration measurements.

Non-Contact Sensor Array Placement

When non-contact sensors are used, a first step is to locate the propagation window on the human's chest as described above. The array is then positioned relative to the human and vibrational cardiac data is collected from measurement locations that are placed within the propagation window.

For purposes of discussing and understanding the embodiments of the invention, it is understood that various terms are used by those knowledgeable in the art to describe methodology, techniques and various alternative approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized and that logical, mechanical, electrical, computational and other changes may be made without departing from the scope of the present invention.

Some portions of the description may be presented in terms of algorithms and symbolic representations of operations on, for example, data bits within a computer memory. These algorithmic descriptions and representations are the means used by those of ordinary skill in the signal analysis and data processing arts to most effectively convey the substance of their work to others of ordinary skill in the art. An algorithm is herein, and generally, conceived to be a self-consistent sequence of acts leading to a desired result. The acts are those requiring physical manipulations of physical quantities. Usually, though not necessarily, these quantities take the form of mechanical, electrical or magnetic signals capable of being acquired, transformed, stored, transferred, combined, compared, and otherwise manipulated. It has proven convenient at times, principally for reasons of common usage, to refer to these signals represented as bits, values, elements, symbols, characters, terms, numbers, waveforms, data, sampled data, time series or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "analyzing" or "processing" or "computing" or "calculating" or "determining" or "displaying" or "measuring" or "acquiring" or "sensing" or "transducing" or the like, can refer to the action and processes of one or more of a computer system, data acquisition system, multi-channel mechanical-to-electrical transducer or similar device, that acquires, manipulates and transforms data represented as physical (electronic) quantities within the computer system's registers and memories into other data similarly represented as physical quantities within the computer system memories or registers or other such information storage, transmission, or display devices.

Apparatuses for performing the operations herein can implement the present invention. These apparatuses may be specially constructed for the required purposes, or it may comprise a set of multiple transducers, general-purpose computer, selectively activated or reconfigured by a computer program stored in the computer. It may also consist of a combination of both a specially constructed device and a program-activated computer. Such a computer program may be stored in a computer readable storage medium, such as, but not limited to, any type of disk including floppy disks, hard disks, optical disks, compact disk read-only memories (CD-ROMs), and magnetic-optical disks, read-only memories (ROMs), random access memories (RAMs), electrically programmable read-only memories (EPROM)s, electrically erasable programmable read-only memories (EESPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct a more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with digital computing system configurations other than those described, including hand-held devices, multiprocessor systems, microprocessor-based or programmable consumer electronics, digital signal processing (DSP) devices, network PCs, cloud services, minicomputers, mainframe computers, parallel computing architectures and the like. The invention can also be practiced in distributed computing environments where tasks are performed by remote processing devices that are linked through a communications network.

The methods of the invention may be implemented using computer software. If written in a programming language conforming to a recognized standard, sequences of instructions designed to implement the methods can be either compiled and/or executed on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, algorithm,), as taking an action or causing a result. Such expressions are merely a shorthand way of saying that execution of the software by a computer causes the processor of the computer to perform a desired action or produce a desired result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing program algorithmic code on a computer, the expression of that technique may be more aptly and succinctly conveyed and communicated as a formula, algorithm, mathematical expression, flow diagram or flow chart. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of non-transitory signals; etc.; which do not encompass any transitory form of signal transmission.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described herein, but can be practiced with modification and alteration within the spirit and scope of the appended claims. The description is thus to be regarded as illustrative instead of limiting.

What is claimed:

1. An apparatus to establish sensor locations on a human's body, comprising:
    a first fixture, the first fixture provides a measurement datum, a first sensor is supported by the first fixture, the first fixture is configured to provide a tensile preload to the first sensor, a first location on the human's body is associated with the first sensor and is established using the measurement datum and the first sensor, the first sensor is configured to sense vibration of the human's body at the first location;
    a second fixture, the second fixture articulates with the first fixture and a second sensor is supported by the second fixture, the second fixture is configured to provide a tensile preload to the second sensor, a second location on the human's body is associated with the second sensor and is established using the measurement datum and the second sensor, the second sensor is configured to sense vibration of the human's body at the second location, the first fixture and the second fixture provide a separation distance between the first sensor and the second sensor; and
    a first measurement indicator, the first measurement indicator to provide location information on the second sensor referenced from the measurement datum, wherein in operation, the first sensor and the second sensor articulate to conform to the human's body and provide signals responsive to vibration of the human's body.

2. The apparatus of claim 1, wherein the first sensor is a film sensor.

3. The apparatus of claim 2, wherein the film sensor is made with polyvinylidene fluoride (PVDF).

4. The apparatus of claim 3, wherein the first fixture in configured to receive a first plurality of sensors and to provide a tensile preload to the first plurality.

5. The apparatus of claim 4, wherein the first plurality is made with PVDF film and the first fixture is configured to provide the tensile preload through an elasticity of the first fixture.

6. The apparatus of claim 5, wherein the first plurality is equal to two or more sensors.

7. The apparatus of claim 5, wherein a threaded member together with the elasticity of the first fixture is used to apply tension to the PVDF film along two opposing sides of the PVDF film.

8. The apparatus of claim 7, further comprising:
    a first corner tensioning device, the first corner tensioning device is configured to apply tension to a first corner of the PVDF film.

9. The apparatus of claim 8, further comprising:
    a second corner tensioning device, the second corner tensioning device is configured to apply tension to a second corner of the PVDF film;
    a third corner tensioning device, the third corner tensioning device is configured to apply tension to a third corner of the PVDF film; and
    a fourth corner tensioning device, the fourth corner tensioning device is configured to apply tension to a fourth corner of the PVDF film.

10. The apparatus of claim 1, wherein a reference frame structure is configured to receive more than one fixture.

11. The apparatus of claim 1, further comprising:
    a third fixture, the third fixture articulates with the first fixture and a third sensor is supported by the third fixture, the third fixture is configured to provide a tensile preload to the third sensor, a third location on the human's body is associated with the third sensor and is established using the measurement datum and the third sensor, the third sensor is configured to respond to vibration of the human's body at the third location, the first fixture and the third fixture provide a separation distance between the first sensor and the third sensor; and
    a second measurement indicator, the second measurement indicator to provide coordinate information on the third sensor referenced from measurement datum, wherein in operation, the first sensor, the second sensor, and the third sensor articulate to conform to the human's body and provide signals responsive to vibration of the human's body.

12. The apparatus of claim 11, wherein each fixture is configured to tension a sheet of PVDF film and the sheet of PVDF film is patterned to provide five sensors.

13. The apparatus of claim 11, wherein at least one of the first measurement indicator and the second measurement indicator provides coordinate information.

14. The apparatus of claim 11, wherein at least one of the first measurement indicator and the second measurement indicator provides coordinate information using a laser.

15. The apparatus of claim 11, wherein at least one of the first measurement indicator and the second measurement indicator measures an angle formed between a fixture and the measurement datum, and the angle is used to calculate coordinate information.

16. The apparatus of claim 15, wherein an articulation angle is formed between the first fixture and the second fixture, the first fixture and the second fixture articulate using a hinged joint.

17. The apparatus of claim 16, wherein the hinged joint is made with a material selected from the group consisting of metal, plastic, vinyl, fiberglass, pvc, leather, rubber, fabric, and a user specified material.

18. An apparatus to establish sensor locations on a human's body, comprising:
   a reference plane structure, the reference plane structure establishes a measurement datum; and
   a plurality of fixtures, each fixture of the plurality contains at least one sensor and provides a tensile preload to the at least one sensor, a first fixture of the plurality is supported by the reference plane structure, a location on the human's body is associated with each sensor, each location on the human's body is established using the measurement datum and a contact point of each sensor, the plurality are articulated together to conform to a shape of the human's body such that, when in use, each sensor is in contact with the human's body, and each location is defined by the measurement datum and the contact point of each sensor.

19. The apparatus of claim 18, wherein there are at least three fixtures in the plurality, each fixture of the plurality further comprising:
   five sensors and each fixture of the plurality provides a tensile preload to the sensors that it supports.

20. The apparatus of claim 18, further comprising:
   a plurality of measurement indicators, each measurement indicator of the plurality of measurement indicators to provide coordinate information on a sensor relative to the reference plane structure.

21. The apparatus of claim 20, wherein at least one measurement indicator of the plurality measures distance.

22. The apparatus of claim 21, wherein at least one measurement indicator of the plurality uses a laser to measure distance.

23. The apparatus of claim 21, wherein at least one measurement indicator of the plurality measures an angle formed between a fixture and the reference plane structure and the angle is used to calculate coordinate information.

24. The apparatus of claim 18, wherein each sensor is a film sensor.

25. The apparatus of claim 24, wherein the film is a piezoelectric film.

26. The apparatus of claim 25, wherein the film sensor is made with polyvinylidene fluoride PVDF.

27. The apparatus of claim 18, wherein the at least one sensor is an accelerometer.

28. The apparatus of claim 18, further comprising:
   at least one ultrasonic sensor, the at least one ultrasonic sensor to provide depth information on an intercostal space between adjacent ribs of the human, wherein the depth information is used to place the plurality of fixtures on the human's chest.

29. The apparatus of claim 18, wherein a fixture of the plurality of fixtures functions as the reference plane structure thereby providing the measurement datum.

30. A method to assemble an apparatus used to establish sensor locations on a human's body, comprising:
   providing an elastic structure having a first end and a second end;
   compressing the first end and the second end such that the first end and the second end move toward one another;
   attaching a polyvinylidene fluoride (PVDF) film sensor to the first end and the second end; and
   reducing the compression in the elastic structure to provide a tensile preload in the PVDF film sensor.

31. The method of claim 30, wherein the compressing is done with a bolt.

32. The method of claim 30, further comprising:
   adjusting tension in the PVDF film sensor by applying a point load to the elastic structure.

33. The method of claim 32, further comprising:
   adjusting tension in the PVDF film sensor by applying a point load to four locations on the elastic structure.

* * * * *